(12) United States Patent
Dimmer et al.

(10) Patent No.: US 7,054,685 B2
(45) Date of Patent: May 30, 2006

(54) METHOD AND APPARATUS FOR REDUCING ELECTROPORATION-MEDIATED MUSCLE REACTION AND PAIN RESPONSE

(75) Inventors: Steve Dimmer, Valley Center, CA (US); Gunter Hofmann, San Diego, CA (US); Daniel Holt, Mira Mesa, CA (US); Gurvinder Nanda, San Diego, CA (US); Edward M. Nolan, San Diego, CA (US)

(73) Assignee: Genetronics, Inc., San Diego, CA (US)

( * ) Notice: Subject to any disclaimer, the term of this patent is extended or adjusted under 35 U.S.C. 154(b) by 199 days.

(21) Appl. No.: 10/215,963

(22) Filed: Aug. 8, 2002

(65) Prior Publication Data

US 2002/0193833 A1 Dec. 19, 2002

Related U.S. Application Data

(62) Division of application No. 09/535,683, filed on Mar. 23, 2000.
(60) Provisional application No. 60/126,953, filed on Mar. 25, 1999.

(30) Foreign Application Priority Data

Mar. 23, 2000 (WO) .............................. PCT/US00/07972

(51) Int. Cl.
*A61N 1/362* (2006.01)

(52) U.S. Cl. ......................................... 607/3
(58) Field of Classification Search .............. 607/2, 607/3, 74, 75, 66, 67; 604/20; 600/547
See application file for complete search history.

(56) References Cited

U.S. PATENT DOCUMENTS

| 4,822,470 A | 4/1989 | Chang | 604/21 |
| 4,970,154 A | 11/1990 | Chang | 604/21 |
| 5,273,525 A | 12/1993 | Hofmann | 604/21 |
| 5,865,787 A | * 2/1999 | Shapland et al. | 604/21 |

OTHER PUBLICATIONS

Daskalov et al., "Exploring New Instrumentation Parameters for Electrochemotherapy: *Attacking Tumors with Bursts of Biphasic Pulses Instead of Single Pulses,*" *IEEE Engineering in Medicine and Biology*, pp. 62–64 (Jan./Feb. 1999).

M. Prausnitz, "The effects of electric current applied to skin: A review for transdermal drug delivery," *Advanced Drug Delivery Reviews*, 18:395–425 (1996).

* cited by examiner

*Primary Examiner*—Jeffrey R. Jastrzab
(74) *Attorney, Agent, or Firm*—Daniel M. Chambers; Douglas C. Murdock; BioTechnology Law Group

(57) ABSTRACT

A method for delivery of an agent to a cell using electroporation is disclosed. The method includes positioning a first electrode and a second electrode such that an electrical signal passed between the first electrode and the second electrode passes through the cell. The method also includes passing an electrical signal between the first electrode and the second electrode, the electrical signal having a frequency greater than about 10 kHz. In one embodiment of the method, the electrical signal has a bipolar waveform. In another embodiment of the method, the electrodes are positioned at a treatment site, e.g., a tumor, for in vivo delivery of an agent.

25 Claims, 19 Drawing Sheets

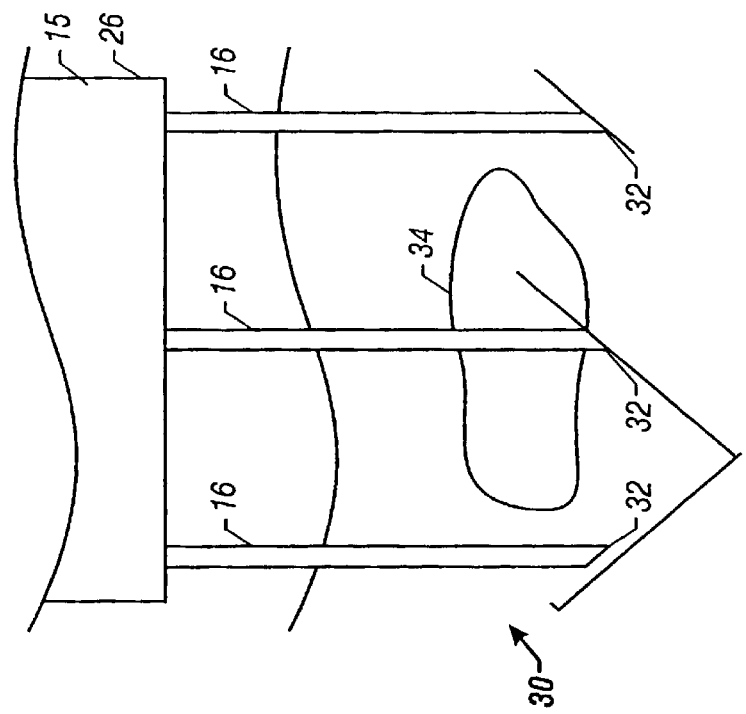
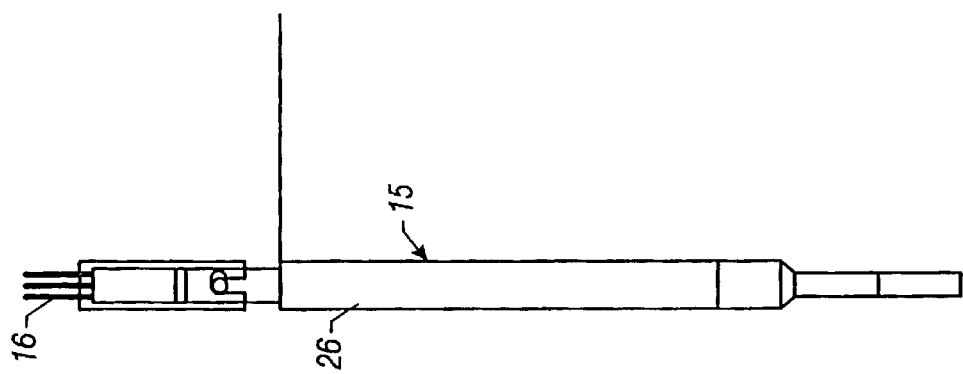

METHOD AND APPARATUS FOR REDUCING ELECTROPORATION-MEDIATED MUSCLE REACTION AND PAIN RESPONSE

This is a divisional of U.S. patent application Ser. No. 09/535,683, filed Mar. 23, 2000, which is a conversion of U.S. Provisional Patent Application No. 60/126,953 and of PCT/US00/07972, filed Mar. 23, 2000, all of which are incorporated disclosure of this application.

RELATED APPLICATION

This application relies for priority under 35 U.S.C. §119 (e)(1) on provisional application Ser. No. 60/126,953, filed Mar. 25, 1999.

FIELD OF THE INVENTION

The present invention relates generally to the use of electric pulses to increase the permeability of cell, and more specifically to a method and electroporation therapy apparatus for the application of controlled electric fields for delivery of agents into cells by electroporation.

BACKGROUND

In the 1970=s it was discovered that electric fields could be used to create pores in cells without causing permanent damage. This discovery made possible the insertion of large molecules into cell cytoplasm. It is known that genes and other molecules such as pharmacological compounds can be incorporated into live cells through a process known as electroporation. The genes or other molecules are mixed with the live cells in a buffer medium and short pulses of high electric fields are applied. The cell membranes are transiently made porous and the genes or molecules enter the cells, where they can modify the genome of the cell.

Electroporation in vivo is often limited to tissue or cells that are close to the skin of the organism where the electrodes can be placed. Therefore, tissue which would otherwise be treatable by systemic drug delivery or chemotherapy, such as a tumor, is generally inaccessible to electrodes used for electroporation. In the treatment of certain types of cancer with chemotherapy, it is necessary to use a high enough dose of a drug to kill the cancer cells without killing an unacceptable high number of normal cells. If the chemotherapy drug could be inserted directly inside the cancer cells, this objective could be achieved. Some of the anticancer drugs, for example, bleomycin, normally cannot penetrate the membranes of certain cancer cells effectively. However, electroporation makes it possible to insert bleomycin into cells.

Treatment typically is carried out by injecting an anticancer drug directly into the tumor and applying electroporation signals between a pair of electrodes positioned on opposite sides of a tumor. The field strength must be adjusted reasonably accurately so that electroporation of the cells of the tumor occurs without damage, or at least minimal damage, to any normal or healthy cells. This can normally be easily carried out with external tumors by applying the electrodes to opposite sides of the tumor so that the electric field is between the electrodes. When the field is uniform, the distance between the electrodes can then be measured and a suitable voltage according to the formula $E=V/d$ can then be applied to the electrodes ($E$=electric field strength in V/cm; $V$=voltage in volts; and $d$=distance in cm). When large or internal tumors are to be treated, it is not easy to properly locate electrodes and measure the distance between them. The aforementioned parent application discloses a system of electrodes for in vivo electroporation wherein the electrodes may be inserted into the tumor. In related U.S. Pat. No. 5,273,525, a syringe for injecting molecules and macromolecules for electroporation utilizes needles for injection which also function as electrodes. This construction enables subsurface placement of electrodes.

DNA immunization, a novel method to induce protective immune responses, was recently introduced into the scientific community and proven to be very effective in animal models. This technology is currently in first safety and efficacy trials in human volunteers. DNA immunization entails the direct, in vivo administration of plasmid-based DNA vectors that encode the production of defined microbial antigens or other desired antigens. The de novo production of these antigens in the host's own cells results in the elicitation of antibody (i.e. humoral) and cellular immune responses that provide protection against live virus challenge, for example, and persist for extended periods in the absence of further immunizations. The unique advantage of this technology is its ability to mimic the effects of live attenuated vaccines without the safety and stability concerns associated with the parenteral administration of live infectious agents. Because of these advantages, considerable research efforts have focused on refining in vivo delivery systems for naked DNA that result in maximal antigen production and resultant immune responses.

The most widely used administration of vaccine DNA is direct injection of the DNA into muscle or skin by needle and syringe. This method is effective in inducing or augmenting immune responses in small animals, as mice, but even here it requires the administration of relatively large amounts of DNA, ca. 50 to 100 ug per mouse. To obtain immune responses in larger animals, as rabbits, non-human primates, and humans, very large amounts of DNA have to be injected. It has to be seen whether this requirement for very large amounts of vaccine DNA turns out to be practical, for safety and commercial reasons, in human applications.

Despite the suitability of the epidermis as a target tissue for gene therapy or DNA vaccination, there are significant barriers to safe, easy, efficient, and economical gene delivery. In particular, the lipid-rich stratum corneum, which is composed of dead keratinocytes surrounded by multiple, parallel bilayer membranes, represents a formidable physical barrier to epidermal gene transfer. To overcome this barrier, a novel, non-viral approach, involving the basic concept of electroporation to introduce genes into the epidermis or muscle is provided by the present invention.

Treatment of a subject using electroporation provides a means for avoiding the deleterious effects typically associated with administration of anticancer or cytotoxic agents. Such treatment would allow introduction of these agents to selectively damage or kill undesirable cells while avoiding surrounding healthy cells or tissue. However, the electrical signals which are typically used for electroporation cause considerable discomfort to a patient. There is often enough discomfort that patients are given general anesthesia before receiving the electroporation treatment.

SUMMARY OF THE INVENTION

The present invention is based on the discovery of apparatuses, instruments and methods for reducing pain often associated with clinical use of electroporation and delivery of agents to cells. The invention provides such apparatus and instruments which allow administration of electric pulses to a patient while reducing the level of discomfort.

In one embodiment, a method of the invention includes positioning a first electrode and a second electrode such that an electrical signal passed between the first electrode and the second electrode passes through the cell. The method also includes passing an electrical signal with a frequency greater than about 10 kHz between the first electrode and the second electrode. In one embodiment of the method, the electrical signal has a bipolar square waveform. In another embodiment of the method, the electrodes are positioned at a treatment site for in vivo delivery of an agent.

The invention also relates to an electroporation instrument for use with an electroporation therapy apparatus having two or more electrodes. The electroporation instrument includes a connector configured to be coupled with the electroporation therapy apparatus. The connector provides electrical communication between the electroporation instrument and the electrodes of the electroporation therapy apparatus. The electroporation instrument also includes electronics for applying an electrical signal to the two or more electrodes. The electrical signal has a frequency greater than about 10 kHz. In one embodiment, the electrical signal has a bipolar square waveform.

One embodiment of the invention includes electronics for applying an electroporation signal to the electrodes of the electroporation therapy apparatus and electronics for applying an agent movement signal to the electrodes of the electroporation therapy apparatus. The agent movement signals can be applied independently of the electroporation signals.

Another embodiment of the electroporation instrument includes electronics for applying therapeutic electrical signals to the plurality of electrodes and electronics for testing whether the electrodes are positioned at the treatment site in an orientation suitable for applying the therapeutic electrical signals to the electrodes. The electroporation instrument can also include electronics for withholding the therapeutic signals if the electrodes are not positioned in an orientation suitable for application of the therapeutic signals.

Yet another embodiment of the electroporation instrument includes electronics for applying an electrical signal having a bipolar waveform to the electrodes of the electroporation therapy apparatus. The electronics include a power source for producing a monopolar electrical signal and polarity changing electronics for changing the monopolar electrical signal to a bipolar electrical signal. Hence, the electroporation instrument can include a single power source for providing bipolar signals.

DESCRIPTION OF THE DRAWINGS

FIG. 2 is a sideview of a electroporation therapy apparatus.

FIG. 3 illustrates the electrodes of an electroporation therapy apparatus positioned at a treatment site.

DETAILED DESCRIPTION OF THE PREFERRED EMBODIMENT

Figure 1:
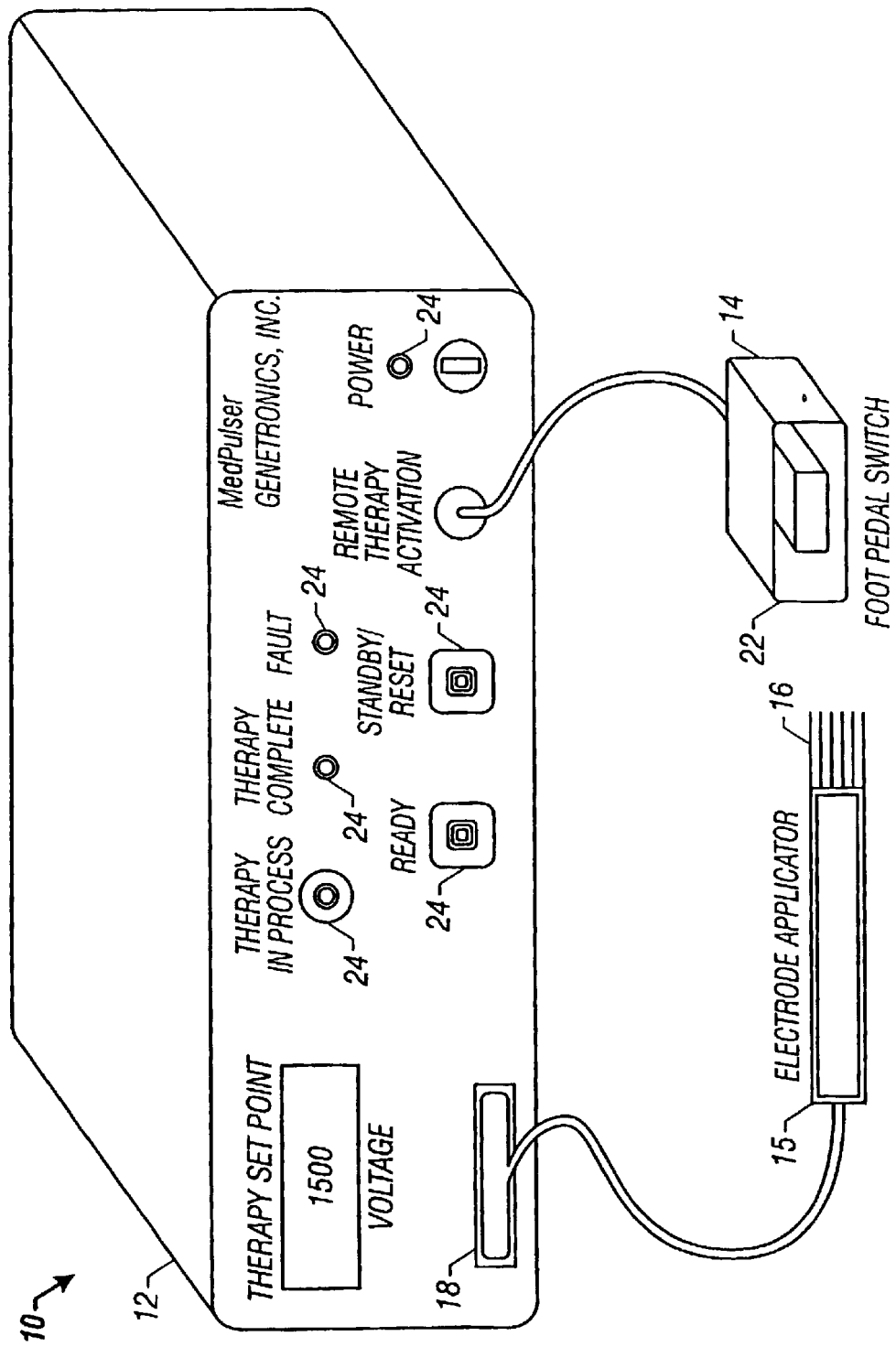
FIG. 1 illustrates an electroporation system according to the present invention.

The present invention provides an instrument and method for the therapeutic application of electroporation. Two or more electrodes are positioned at a treatment site such that a therapeutic electrical signal passed between the electrodes passes through the treatment site. One or more therapeutic electrical signals are then passed between the electrodes. A therapeutic agent can be introduced to the treatment site before, after and/or during the passage of the therapeutic electrical signals between the electrodes. The therapeutic electrical signal can include an electroporation signal and/or an agent movement signal. The electroporation signal creates pores in the cells located at the treatment site. The agent can then enter the cells through the pores. The agent movement signals can enhance the opportunity for the agent to enter the cells by providing movement of the agent relative to the cells. The method and instrument are configured to reduce the amount of discomfort experience by the patient during the delivery of the therapeutic electrical signals to the treatment site.

One embodiment of the invention relates to an electroporation instrument for use with an electroporation therapy apparatus having two or more electrodes for positioning at a treatment site. The electroporation instrument includes a connector configured to be coupled with the electroporation therapy apparatus. The connector provides electrical communication between the electroporation instrument and the electrodes of the electroporation therapy apparatus. The electroporation instrument also includes electronics for applying an electroporation signal to the two or more electrodes. The electroporation signal has a bipolar square waveform and a frequency greater than about 10 kHz.

Experimental results illustrate that a patient's level of tolerance to electrical signals increases as the frequency of the electrical signal increases. As a result, the use of electroporation signals having a frequency greater than about 10 kHz reduces the level of discomfort to a patient.

In one embodiment of the invention, the electroporation signals have a bipolar waveform. In another embodiment, the signals have a bipolar square waveform. Prior electroporation signals have a monopolar square waveform. A Fourier transform of these waveforms shows that the monopolar square waveform includes a strong low frequency component which is not present in the bipolar square waveform. As discussed above, low frequency signals cause an increased level of discomfort to the patient. Since the bipolar square waveform is missing the low frequency components present in the monopolar square waveform, the bipolar square waveform reduces the discomfort to a patient below what can be achieved with prior electroporation signals. This discomfort reduction is further reduced by delivering electroporation signals having a bipolar square waveform and a frequency greater than about 10 kHz. The use of the bipolar waveform has the additional advantage of reducing electrode corrosion from what results when a monopolar signal is applied.

One aspect of the electroporation instrument includes electronics for testing whether the electrodes are positioned at the treatment site in an orientation suitable for applying the electroporation signals to the electrodes. For instance, the electronics can test whether the electrodes are positioned too close to a metal implement to safely deliver electroporation signals. For instance, if two electrodes are positioned too close to one another, there is a danger of arcing between the electrodes when the electroporation signals are applied. As a result, the electrodes would not be positioned in an orientation suitable for application of the electroporation signals to the electrodes. The electroporation instrument can include electronics for withholding the electroporation signals when the electrodes are determined to be positioned in a configuration which is not suitable for application of the electroporation signals. As a result, the electroporation instrument increases a patient's comfort level by preventing a patient from experiencing discomfort associated with electrodes being positioned in an orientation which is not suitable for application of the electroporation signals.

The electroporation system 10 includes an electroporation instrument 12, a remote controller 14 and an electroporation therapy apparatus 15 having a plurality of electrodes 16. The electroporation instrument 12 includes a connector 18 for coupling the electroporation instrument 12 to an electroporation therapy apparatus 15. The electroporation instrument 12 includes electronics for applying therapeutic electrical signals to the electrodes 16 of the electroporation therapy apparatus 15. The therapeutic electrical signals can include electroporation signals and/or agent movement signals.

The electroporation instrument 12 also includes a remote controller connector 20 for coupling the remote controller 14 with the electroporation instrument 12. The remote controller 14 allows a user to control one or more functions of the electroporation instrument 12 without touching the electroporation instrument 12. A suitable remote controller 14 is a foot pedal switch 22 for activating pulses to the electrode applicator. The foot pedal switch 22 permits a physician to activate the electroporation instrument 12 while freeing both hands for positioning of the electrode applicator in a patient's tissue.

The electroporation instrument 12 can also include one or more user interfaces 24 for indicating the instrument conditions to an operator. For instance, the user interfaces can indicate when a fault condition is detected, when the electroporation therapy is in process, when the electroporation therapy is complete, and when the electroporation instrument is in standby. Suitable user interfaces include, but are not limited to LEDs, displays 66 for providing a readable message and a speakers for providing an audible message.

FIG. 2 illustrates an electroporation therapy apparatus 15 according to the present invention. The electroporation therapy apparatus 15 includes a body 26 and a plurality of electrodes 16. Although three electrodes are illustrated, the electroporation therapy apparatus can include as few as two electrodes. An electroporation therapy apparatus having more than two electrodes can have the electrodes 16 positioned in an array. Suitable arrays include, but are not limited to, a square array, a circular array, and a hexagonal array. The electrodes 16 in an array can be evenly spaced or can have different spacing. Further, an embodiment of the electroporation therapy apparatus 15 includes a plurality of electrodes 16 without a body 26. In this embodiment the electrodes 16 can be moved independently of one another.

The electrodes can have a variety of configurations including, but not limited to, a caliper that grips the epidermis overlying a region of cells to be treated. Additionally, one or more of the electrodes 16 can include a tissue piercing distal end 32 to aid in positioning the electroporation therapy apparatus at a treatment site. The tissue piercing distal end aids in penetrating tissues between the skin and the treatment site 30. See U.S. Pat. Nos. 6,014,584; 6,009,347; 6,009,345; 5,993,434; 5,994,710; 5,702,359, for exemplary electrodes, herein incorporated by reference.

FIG. 3 illustrates the electrodes 16 of an electroporation therapy apparatus 15 positioned at a treatment site 30 of a patient. The illustrated treatment site 30 includes a tumor 34 which is to receive the electroporation treatment. The electrodes 16 are preferably positioned such that therapeutic electrical signals passed between two or more of the electrodes 16 pass through the tumor 34 in order to expose at least a portion of the cells within the tumor 34 to the therapeutic electrical signal. Correct positioning of the electroporation therapy apparatus 15 can include positioning all or a portion of the electrodes 16 on the skin surface while positioning the remaining electrodes 16 subcutaneously. Alternatively, all the electrodes can be positioned subcutaneously. The positioning of the electrodes will depend on the position, size and accessibility of the treatment site 30.

Although FIG. 3 illustrates employment of the electroporation therapy apparatus 15 in vivo situation, the electroporation therapy apparatuses 14, systems and methods according to the present invention can be similarly employed in vitro. Hence, the treatment site need not be in a patient and in some embodiments can be an in vitro treatment site.

The electroporation instrument 12 includes electronics for applying therapeutic electrical signals to the electrodes 16 of the electroporation therapy apparatus 15. As described above, the therapeutic electrical signals include electroporation and/or agent movement signals. The electroporation signals serve to temporarily create pores in the cells of the treatment site 30 without causing permanent cell damage. One or more agents, such as genes and/or drugs, can be delivered to the treatment site 30 before, after or during the application of the therapeutic electrical signals. These agents can enter the cells within a treatment site 30 through the pores created by the electroporation signals.

The agent movement signals cause movement of an agent relative to cells. Certain agents in suspension are known to move through the suspension in response to application of an electric field. The agent movement signals provides the electric field which provides motion to the agents. This movement is generally in a particular direction relative to the applied field. Due to the size difference between cells and the agent, this movement can drive an agent toward a cell. When electroporation signals have created pores in the cell, the movement of the agent increases the opportunity for the agent to enter the cell though the opening. As a result, the agent movement signals can increase the efficiency of an electroporation treatment.

Application of electrical signals between the electrodes 16 can cause a patient considerable discomfort characterized by pain and involuntary muscle response. Previous studies of patient tolerance to electrical signals show that a patient's tolerance to a sinusoidal electrical current delivered to the body increases with an increase in the frequency. For instance, at a frequency of about 10 kHz, a patient typically perceives the current at about 2 mA while at a frequency of about 100 kHz, the current must be increased to about 40 mA before the patient perceives the current. At frequencies above about 100 kHz, the heat from the induced electric field is perceived before the shock from the electric field is perceived. One embodiment of the present invention is directed toward applying electroporation signals with reduced low frequency components to reduce the discomfort to the patient.

Figure 4A:
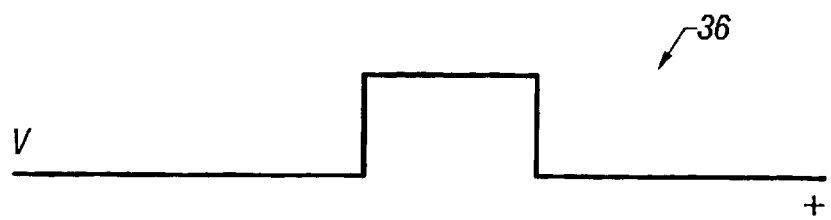
FIG. 4A illustrates an electroporation signal used in prior art electroporation treatments.
Figure 4B:
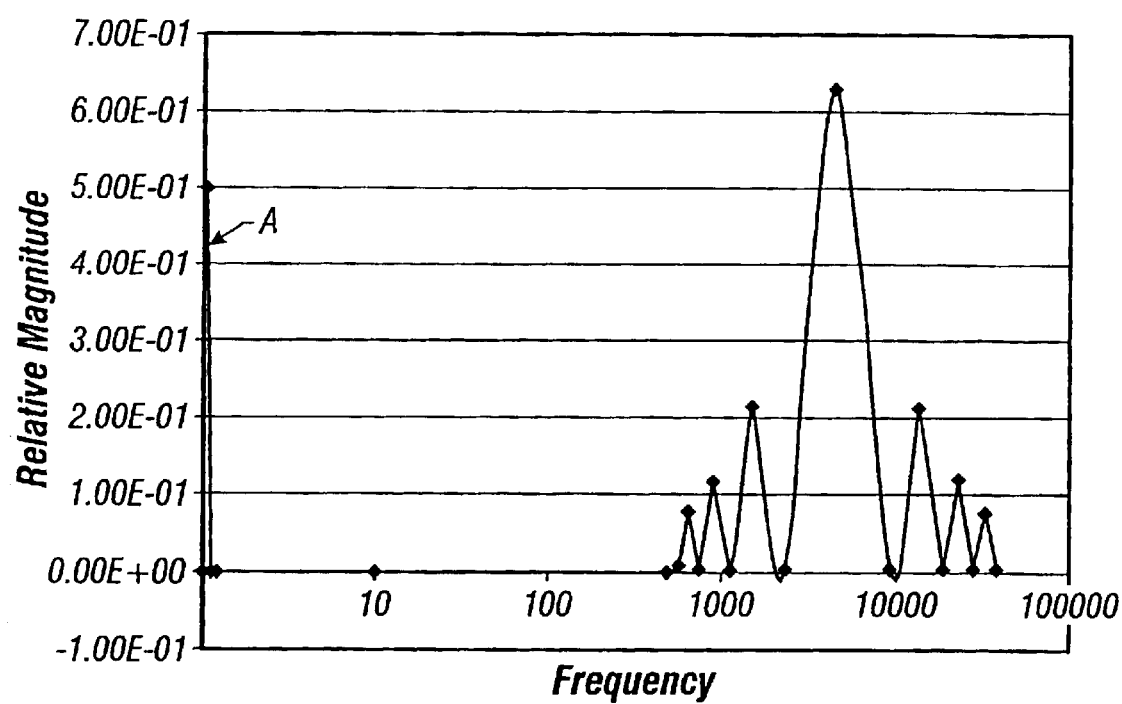
FIG. 4B is a Fourier transform of the electroporation signal illustrated in FIG. 4A.

A common electroporation signal which is typically used for in-vitro electroporation treatments has a monopolar square waveform 36 as illustrated in FIG. 4A. FIG. 4B shows the Fourier transform of a monopolar square wave. The Fourier transform shows the relative amplitude of the various sinusoidal wave component which make up the monopolar square wave. The Fourier transform illustrates that there is a strong low frequency component to the monopolar square waveform 36. This low frequency component is illustrated by the arrow labeled A. As described above, patient discomfort increases as the signal frequency decreases. Accordingly, the inventors believe that strong low frequency component in the monopolar square wave is responsible for a large portion of the patient discomfort associated with the monopolar square waveform 36.

Figure 5A:
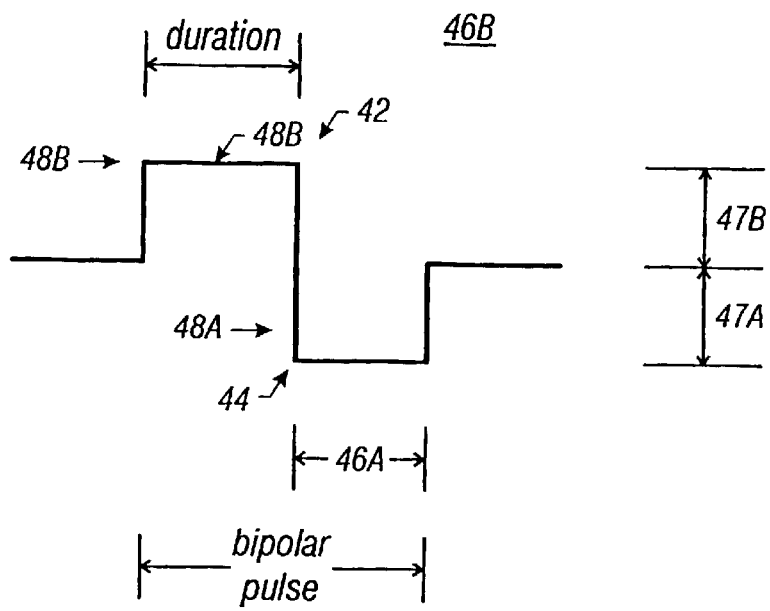
FIG. 5A illustrates an electroporation signal including a bipolar square pulse.
Figure 5B:
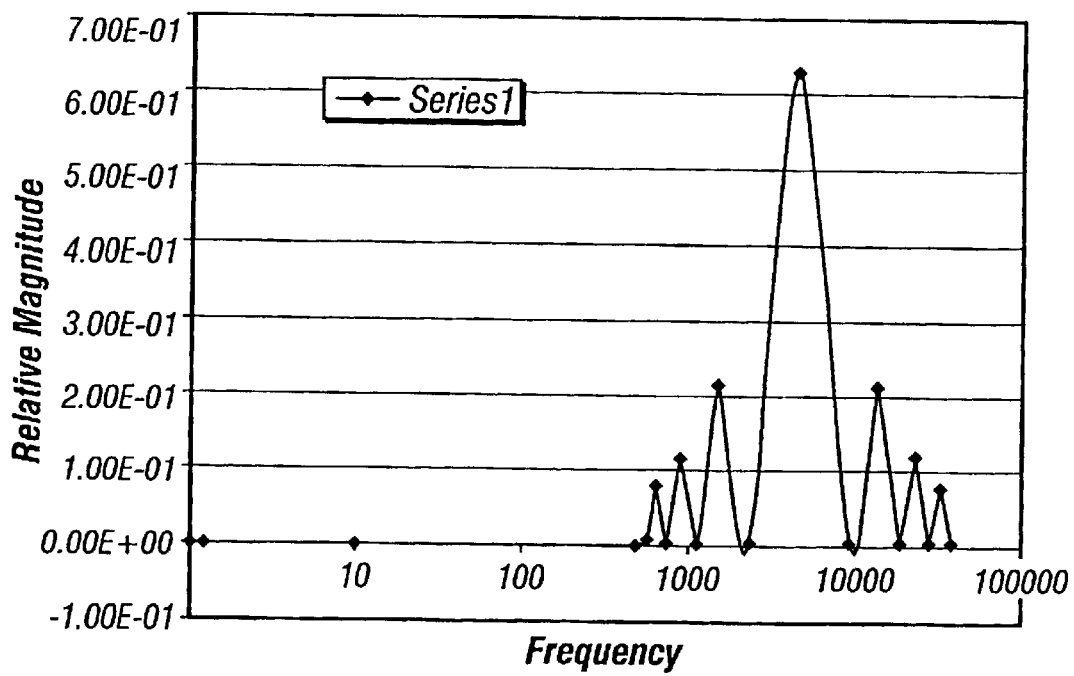
FIG. 5B is a Fourier transform of the electroporation signal illustrated in FIG. 5A.

The electroporation signals according to the present invention preferably have a bipolar square waveform 42 such as the bipolar pulse 44 illustrated in FIG. 5A. FIG. 5B provides the Fourier transform for the bipolar square waveform illustrated in FIG. 5A. The low frequency component present in FIG. 4B is not present in the Fourier transform of FIG. 5B. As described above, the low frequency component is responsible for discomfort to the patient. Since the bipolar square waveform does not include this low frequency component, the bipolar square waveform reduces the discomfort of the electroporation signals.

The electroporation signal illustrated in FIG. 5A has a first polarity duration 46A and a first polarity peak potential 47A associated with a first polarity 48A. Additionally, the electroporation signal includes a second polarity duration 46B and a second polarity peak potential 47B associated with a second polarity 48B. Although the preferred electroporation signal has a bipolar square waveform, the present invention is not limited to these waveforms. For instance, suitable electroporation signal waveforms include, but are not limited to, monopolar, triangular, circular, sinusoidal and exponential waveforms. To illustrate this point FIG. 6 illustrates the a first polarity duration 46A, first polarity peak potential 47A, second polarity duration 46B and a second polarity peak potential 47B of a bipolar sinusoidal waveform.

Figure 6:
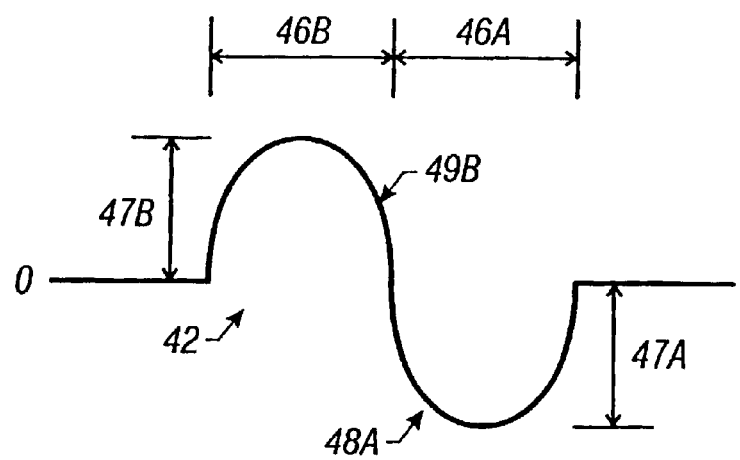
FIG. 6 illustrates a bipolar sinusoidal waveform according to the present invention.
Figure 7A:
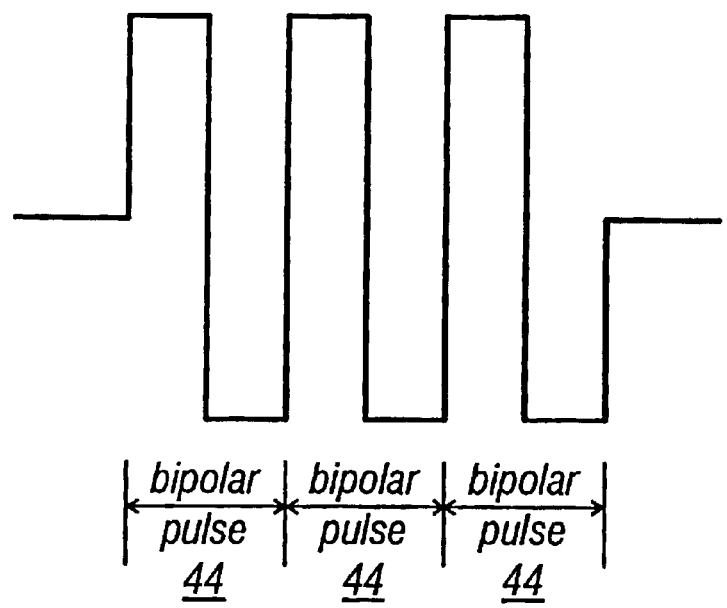
FIG. 7A illustrates an electroporation signal including a bipolar pulse sequence.
Figure 7B:
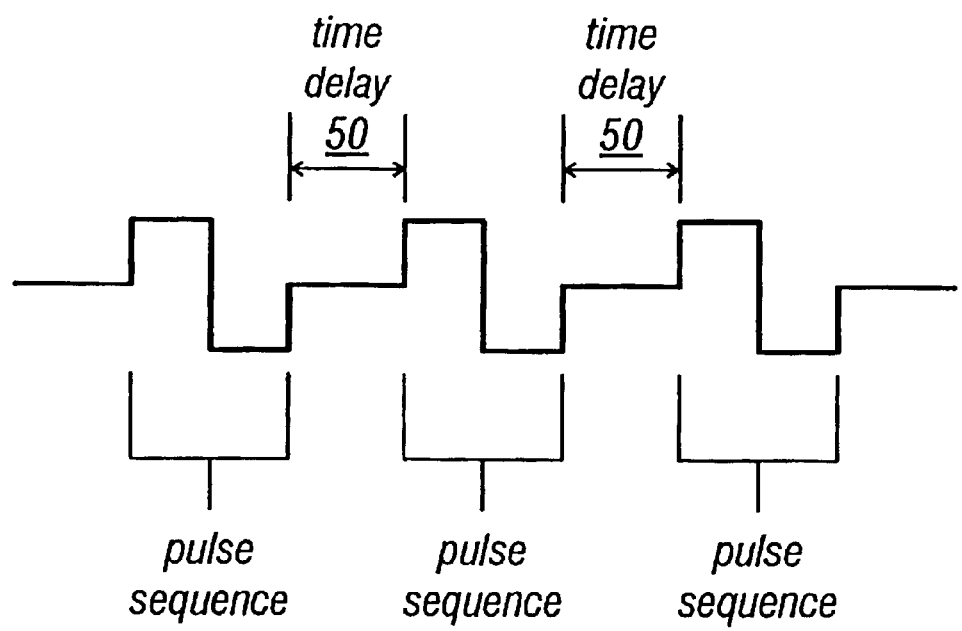
FIG. 7B illustrates a time delay between electroporation signals.
Figure 7C:
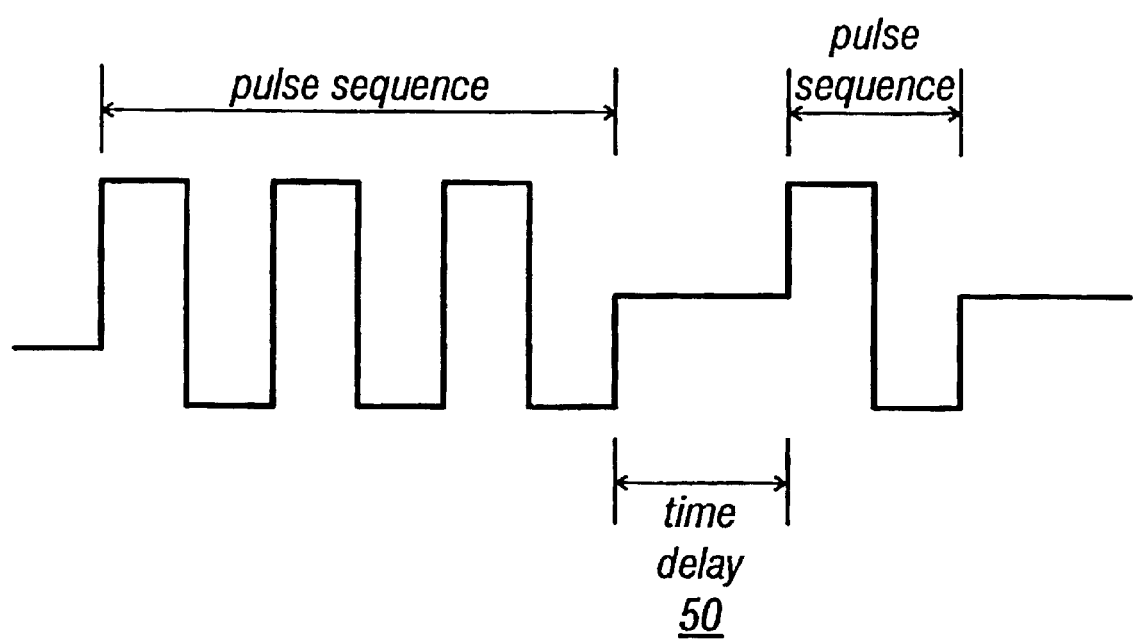
FIG. 7C illustrates a time delay between different signals where the electroporation signals are different from one another.

The electroporation signal can include a single bipolar pulse as illustrated in FIG. 5A and FIG. 6 or can include a bipolar pulse sequence as illustrated in FIG. 7A. Further, an electroporation therapy treatment can include application of several electroporation signals separated by a time delay as illustrated in FIGS. 7B and 7C. The time delay is preferably greater than the relaxation time of muscle. A time delay greater than the time delay of muscle allows the muscle to relax after receiving the electroporation signal. Hence, cumulative effects of the electroporation signals on the muscle are avoided. The time delay is preferably 0 to 200 ms and is more preferably 5 ms to 100 ms and most preferably 20 ms to 80 ms. The characteristics of the electroporation signal delivered before and after the time delay can be same or can be different. For instance, one electroporation signal may have a longer duration or a higher peak potential than another electroporation signal. Finally, the time delay between different electroporation signals can be zero.

The efficiency of delivering an agent to cells can be increased by moving the agent relative to the cells. This movement increases the opportunity for an agent to enter a cell through a pore created by the electroporation signals. Because a variety of agents are known to move through a fluid in response to application of an electric field, the movement can be achieved by creating a net potential at a treatment site during an electroporation therapy treatment. A net potential means that during application of an electroporation signal to a treatment site, the potential applied while the electroporation signals is in the first polarity does not offset the potential applied while the electroporation signal is in the second polarity. For instance, if the first polarity duration of the bipolar pulse illustrated in FIG. 5A was the same as the second polarity duration and the first polarity peak potential was the same as the second polarity peak potential, the potential applied during the second polarity duration would offset the potential applied during the first polarity duration. Hence, there would be zero net potential.

Figure 7D:
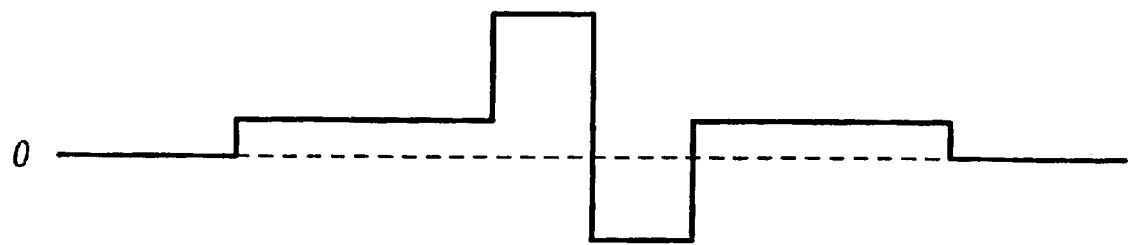
FIG. 7D illustrates a therapeutic signal including an agent movement signal and a electroporation signal.

FIG. 7D illustrates a therapeutic signal which provides a net potential within a treatment site. The therapeutic signal includes an agent movement signal combined with an electroporation signal. The agent movement signal is a monopolar signal having a substantially constant potential. Hence, the agent movement signal provides a D.C. offset to the electroporation signal. The agent movement signal provides a net potential both before, after and during the electroporation signal is applied. Accordingly, movement of the agent is achieved before and after creation of the pores in the cells. Although a single electroporation signal is illustrated during application of the agent movement signal, a plurality of electroporation signals can be applied during a single agent movement signal. Further, although the agent movement signal is shown being applied before, after and during the delivery of the electroporation signal, the agent movement signal can be applied before and/or after the application of the electroporation signal.

Figure 7E:
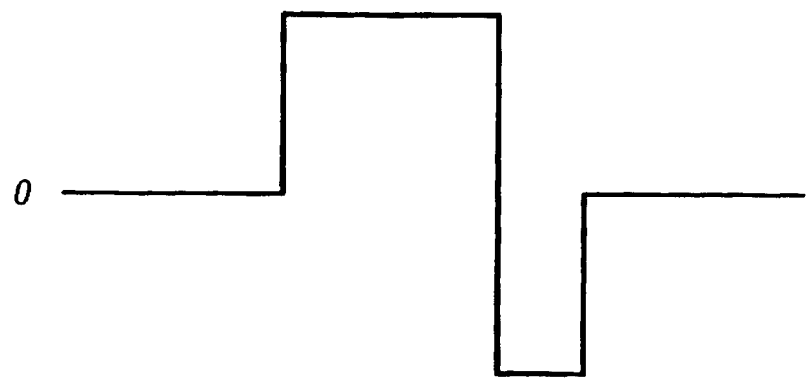
FIG. 7E illustrates an electroporation signal which provides a net potential during an electroporation therapy treatment.

FIG. 7E illustrates an embodiment of an electroporation signal which provides a net potential. The first polarity peak potential 47A is the same as the second polarity peak potential 47B but the second polarity duration 46B is longer than the first polarity duration 46A. As a result, the first polarity peak potential 47A does not offset the second polarity peak potential 47B and there is a net potential.

Figure 7F:
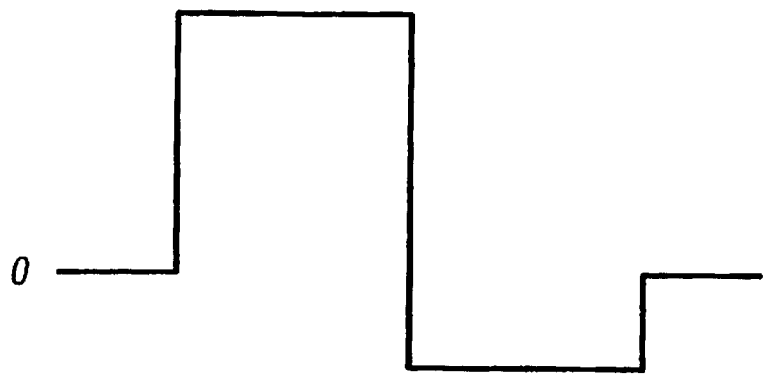
FIG. 7F illustrates another embodiment of an electroporation signal which provides a net potential during an electroporation therapy treatment.

FIG. 7F illustrates another embodiment of an electroporation signal provides a net potential. The first polarity duration 46A is the same as the second polarity duration 46B but the first polarity peak potential 47A is less than the second polarity peak potential. Since the first polarity duration 46A is the same as the second polarity duration 46B, the first polarity peak potential does not offset the second polarity peak potential and there is a net potential. The Fourier transforms of FIG. 7E and FIG. 7F show that these waveforms can be developed by adding DC components to a bipolar square wave.

Figure 7G:
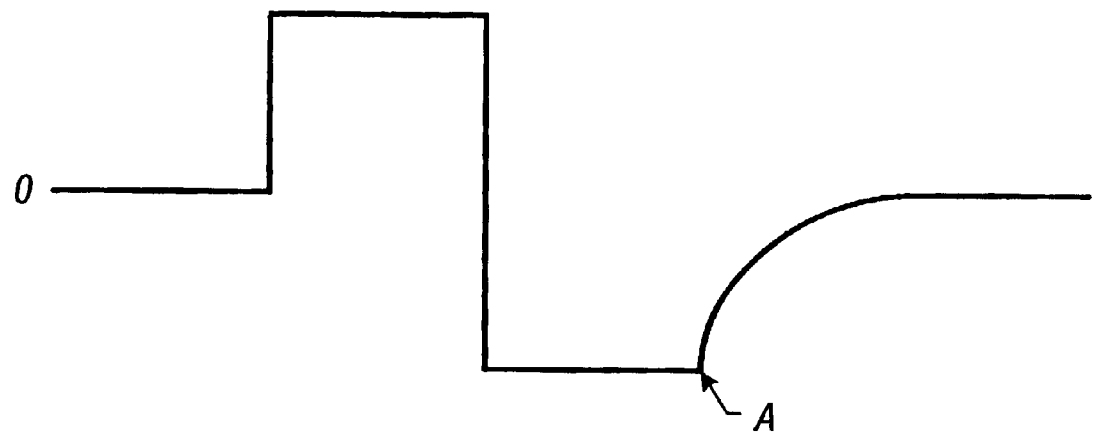
FIG. 7G illustrates a net potential which results from terminating an electroporation signal without driving the potential of the electroporation signal to zero.

Agent movement can be achieved by not driving the electroporation to zero potential. FIG. 7G illustrates the potential within a treatment site during application of an electroporation signal. At the point labeled A, the electroporation signal is stopped without driving the potential to zero. The cells within a treatment site have a capacitive effects. Hence, once application of the electroporation signal is stopped without driving the potential to zero, the cells discharge leaving the tail illustrated in FIG. 7G. This tail provides net potential within the treatment site and accordingly provides movement of an agent within the treatment site.

Other electroporation signals which can provide agent movement include electroporation signals where the second polarity duration 46B is different from the first polarity duration 46A and the second polarity peak potential 47B is different from the first polarity peak potential 47A.

The discomfort to the patient is further reduced by increasing the frequency of the electroporation signal. The frequency is related to the first polarity duration 46A and the second polarity duration 46B as illustrated by Equation 1.

$$\text{Frequency}=1/(\text{First polarity duration}+\text{Second polarity duration}) \quad (1)$$

The frequency refers to the frequency of the pulses within an electroporation signal. Since a single electroporation treatment can employ different electroporation signals, an electroporation therapy can include electroporation signals having different frequencies.

Experimental data shows that as the frequency of electroporation signals having a bipolar square waveform increases, the patients have an increased tolerance to the induced electric field (see Example 1). The frequency is preferably greater than about 10 kHz, more preferably at least about 40 kHz, even more preferably at least about 100 kHz and most preferably at least about 500 kHz. In one embodiment, the frequency is less than about 10 MHz, in another embodiment, the frequency is about 40 kHz-1 MHz and in yet another embodiment the frequency is about 100 kHz-500 kHz and in still another embodiment the frequency is greater than about 200 kHz and at most about 500 kHz.

Equation 1 illustrates that increased frequency is associated with a reduced pulse duration. Therapeutic electrical signals according to the present invention preferably have a pulse duration of less than about 50 μs, more preferably have a pulse duration of less than about 12.5 μs and most preferably a pulse duration of less than about 5 μs. In one embodiment of the invention, the pulse duration is about 80 ns–50 μs and in another embodiment of the invention the pulse duration is about 2 μs–50 μs.

The efficiency of cell electroporation increases as the energy field between the electrodes 16 increases. The energy field created between two electrodes 16 can be determined according to Equation 2, where E is the electric field, V is the potential between the two electrodes 16, r is the diameter of an electrode and D is the displacement between the electrode centers.

$$E=V/(2r\ ln(D/r)) \quad (2)$$

Delivery of the electroporation signals preferably includes creating an energy field of at least about 25 V/cm and more preferably at least about 100 V/cm between two of the electrodes 16 of the electroporation therapy apparatus 15. In one embodiment of the invention, delivery of the electroporation signals includes creating an energy field of about 100 V/cm–10 kV/cm. Another embodiment includes creating an energy field of about 1 kV/cm-3 kV/cm and yet another includes creating an energy field of about 1 kV/cm-2 kV/cm.

The electroporation signals preferably are delivered with an energy field of at least about 25 V/cm and more preferably at least about 100 V/cm between at least two of the electrodes 16 of the electroporation therapy apparatus 15. In one embodiment of the invention, the energy field during delivery of the electroporation signals is about 100 V/cm–10 kV/cm. In another embodiment, the energy field during delivery of the electroporation signal is about 1 kV/cm-3 kV/cm and in another about 1 kV/cm-2 kV/cm.

As the electric field increases, the total electroporation signal duration can be decreased in order to prevent excessive amounts of energy from being delivered to the treatment site 30. The total electroporation signal duration is the sum of the first polarity durations and the second polarity durations of each electroporation signal included in a single electroporation therapy treatment. The total electroporation signal duration is preferably less than about 10 seconds, more preferably about 30 μs–10 seconds, even more preferably about 30 μs–1 ms and most preferably about 50 μs–400 ms. When the electroporation signals include pulses, the total number of bipolar pulses is preferably 1 to 1,000,000.

To achieve these electric fields within treatment sites 30 including tumors 34 having typical dimensions, the electroporation signal preferably has a peak potential of less than 10 kV, more preferably at least 500 V and most preferably at least 10 V. In one embodiment of the invention, the electroporation signal has a peak potential of 500 V-10 kV and in another embodiment the electroporation signal has a peak potential of about 1 kV-5 kV and in yet another embodiment the electroporation signal has a peak potential of about 1 kV-3 kV. When the electroporation signal has a square waveform, the peak potential is the potential of the signal during the electrical pulse.

Figure 8:
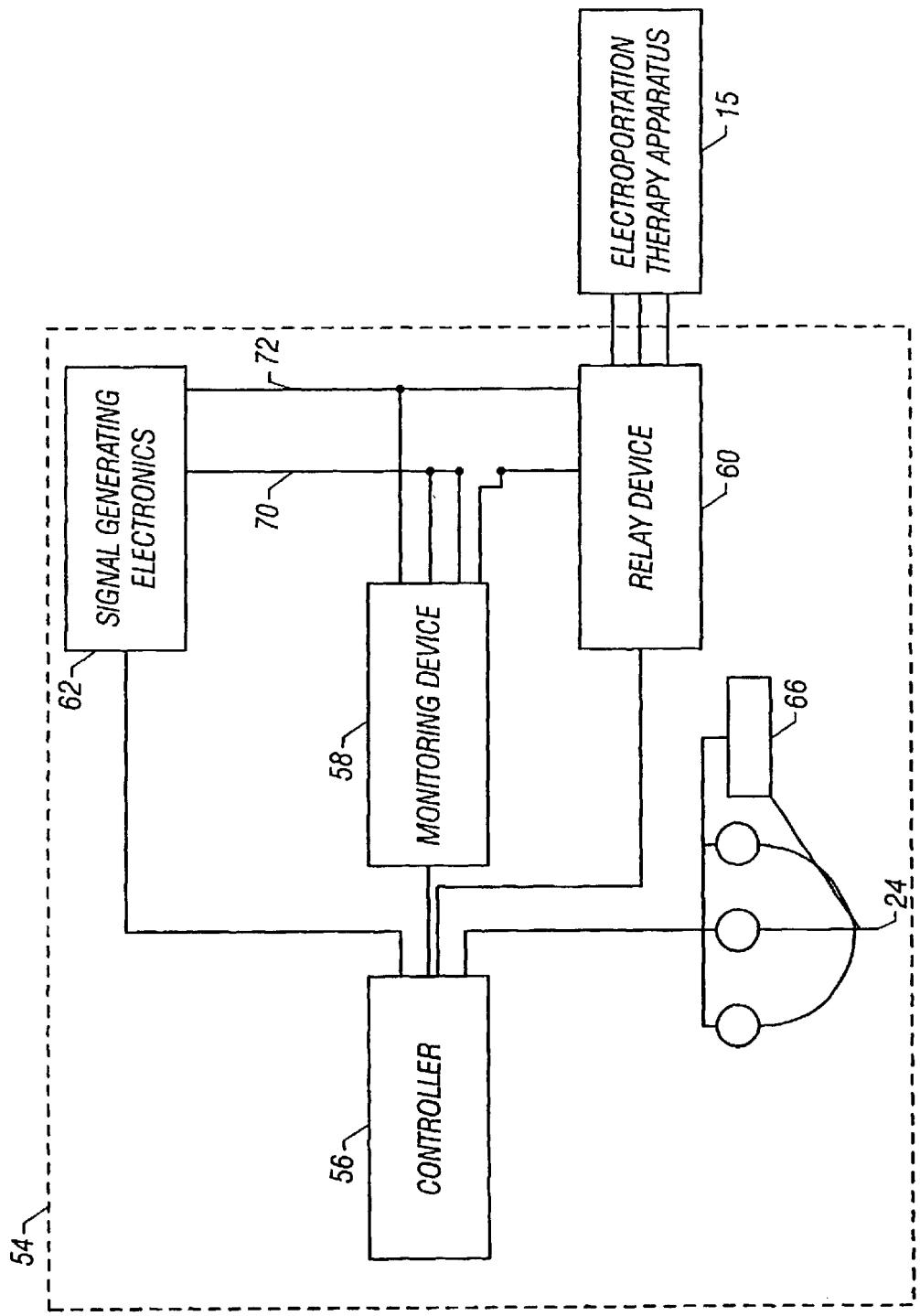
FIG. 8 is a block diagram of the electronics included in an electroporation instrument according to the present invention.

FIG. 8 is a block diagram of electronics 54 included in the electroporation instrument 12 according to the present invention. The electronics 54 includes a controller 56 in communication with a monitoring device 58, a relay device 60, signal generating electronics 62 and one or more user interfaces 24 such as LEDs and/or a display 66. The controller 56 can include one or more processors. Suitable processors include, but are not limited to, microprocessors, a digital signal processors (DSP), integrated circuits, application specific integrated circuits (ASICs), logic gate arrays and switching arrays. The controller 56 can also include one or more memories for storing instructions to be carried out by the one or more processors and/or for storing data developed during operation of the electroporation instrument 12. Suitable memories include, but are not limited to, RAM and electronic read-only memories (e.g., ROM, EPROM, or EEPROM).

The signal generating electronics 62 produce the therapeutic signal on a first output line 70 and a second output line 72. The relay device 60 is coupled with the first output line 70 and the second output line 72 and distributes the therapeutic signals to the electrodes 16 of the electroporation therapy apparatus 15. The controller 56 can operate the relay device 60 to select the electrodes 16 to which the therapeutic electrical signals are applied. As a result, the electrodes 16 to which the therapeutic electrical signals are applied can be changed and/or alternated during the application of the therapeutic electrical signals. Additionally, the number of electrodes 16 to which the therapeutic electrical signal is concurrently applied can be increased or decreased.

The monitoring device 58 is coupled with the first output line 70 and the second output line 72 and monitors the therapeutic signals applied to the electrodes 16. The monitoring device 58 includes a voltage monitor for determining the potential of the signal provided to the electrodes 16. An accurate measure of the potential is obtained by measuring the potential on the first output line 70 and the second output line 72 and then subtracting the two measurements. The monitoring device 58 also includes a current measuring device for measuring the current of the therapeutic electrical signals.

The controller 56 can provide feedback control such as adjusting the therapeutic signals provided by the signal generating electronics 62 in response to measurements generated at the monitoring device 58. For instance, if the controller 56 detects a fault condition, the controller 56 can stop the delivery of the therapeutic electrical signals.

The controller 56 can test the placement of the electrodes 16 after the electrodes 16 are positioned at a treatment site 30 but before the therapeutic electrical signals are delivered. For instance, the controller 56 can determine whether the electrodes 16 are positioned at the treatment site 30 in an orientation suitable for applying the therapeutic electrical signals to the electrodes 16. One example of such a test includes a determination of whether the electrodes 16 are positioned sufficiently far apart from a metal implement such as another electrode or a medical instrument. Because the electrodes 16 can be flexible, they can bend during insertion into the treatment site 30. Due to this bending, the ends of two or more electrodes 16 can approach one another and even cross during the insertion of the electrodes 16 into the treatment site 30. When the electrodes 16 become too close, arcing between the electrodes 16 can occur during the delivery of the therapeutic signals. As a result, if this test indicates that the electrodes 16 are too close to one another, a user interface can be used to indicate this condition to the operator of the electroporation instrument 12. Additionally, the signal producing electronics can be temporarily disabled until the operator has an opportunity to remedy the situation.

A test to determine electrode proximity to metal implements can be performed by applying a first diagnostic signal to the electrodes 16 after the electrodes 16 are positioned at the treatment site 30. The first diagnostic signal preferably has a lower potential than the therapeutic signals since the first diagnostic signal is being used to determine whether the therapeutic signals might arc. The first diagnostic signal can have any potential but preferably has a potential less than about 50 V to reduce discomfort to the patient. The current and potential can be measured in order to determine the resistance to the first diagnostic signal. If the resistance is below a threshold resistance, one or more of the electrodes 16 are determined to be too close to a metal implement and a user interface 24 can be activated to alert the operator to this condition. If the resistance is above the resistance threshold, the electrodes 16 are determined to be properly positioned relative to metal implements and the treatment can continue.

Although resistance is used in the above example of a test for determining whether an electrode is too close to a metal implement, any electrical characteristic which varies as a result of the displacement between an electrode and a metal implement can be employed. Suitable electrical characteristics include, but are not limited to, current and power dissipated by the treatment site 30.

Another test includes measuring the degree of contact between each electrode and the treatment site 30 to determine whether the degree of contact between each electrode and the treatment site 30 is sufficient for conduction of the therapeutic signals. A number of possible treatment sites 30, such as sites within the esophagus, can be difficult to reach. Accordingly, it may be difficult to achieve the desired degree of contact between each electrode and the treatment site 30. Without the proper degree of contact, the treatment site 30 will not receive the desired signals from the electrodes 16. As a result, if this diagnostic test indicates an insufficient degree of contact between an electrode 16 and the treatment sites 30, a user interface 24 can be activated to indicate this condition to the operator of the electroporation instrument 12. Additionally, the signal producing electronics can be temporarily disabled until the operator has an opportunity to remedy the situation.

A test to determine a degree of contact between each electrode and the treatment site 30 can be performed by applying a second diagnostic signal to the electrodes 16 after the electrodes 16 are positioned at the treatment site 30. A suitable second diagnostic signals includes, but is not limited to, a monopolar signal and a bipolar signal. The second diagnostic signal can have any potential but preferably has a potential on the order of the potential of the electroporation signals. The current and potential can be measured in order to determine the current through the treatment site 30. If the current is less than a current threshold, there is determined to be insufficient contact between one or more of the electrodes 16 and the treatment site 30. If the current is above the current threshold, there is determined to be sufficient contact between each of the electrodes 16 and the treatment site 30 and the electroporation treatment is allowed to continue.

Although the current is used in the above example of a test for determining whether the degree of contact between the electrodes 16 and the treatment site 30 is sufficient, any electrical characteristic which varies as a result of the degree of contact between an electrode and a treatment site 30 can be employed. Suitable electrical characteristics include, but are not limited to, resistance and power dissipated by the treatment site 30.

In one embodiment of the invention, the first diagnostic signal and the second diagnostic signal are the same signal. As a result, both tests can be performed using a single signal. In another embodiment of the invention, one or more therapeutic electrical signals serve as the second diagnostic signal. Since delivering the therapeutic electrical signals while there is insufficient contact between an electrode and the treatment site does not cause unusual discomfort or danger to the patient, the therapeutic electrical signals can be delivered and can serve as the second diagnostic signal. In this embodiment, an operator is informed of the insufficient contact during or after the delivery of the therapeutic electrical signals.

When the above testing indicates that the electrodes 16 are positioned at the treatment site 30 in an orientation suitable for applying the therapeutic electrical signals to the electrodes 16, this condition can be indicated to the operator with one of the user interfaces such as an LED. This user interface indicates that the electroporation instrument 12 is ready to deliver the therapeutic electrical signals to the treatment site 30. For instance, this user interface 24 indicates that activating the remote controller 14 will deliver the therapeutic signals.

Alternatively, the above tests can be automatically performed before delivery of the therapeutic electrical signals and the operator is informed when problems in the orientation of the electrodes are detected. Additionally, as described above, testing for degree of contact between an electrode and a treatment site can be performed before, during or after the application of the therapeutic electrical signals. Hence, a user interface can indicate insufficient contact between an electrode and the treatment site after or during delivery of the therapeutic electrical signals. The operator can then re-position the electrodes and make a second effort to apply the therapeutic electrical signals.

Figure 9:
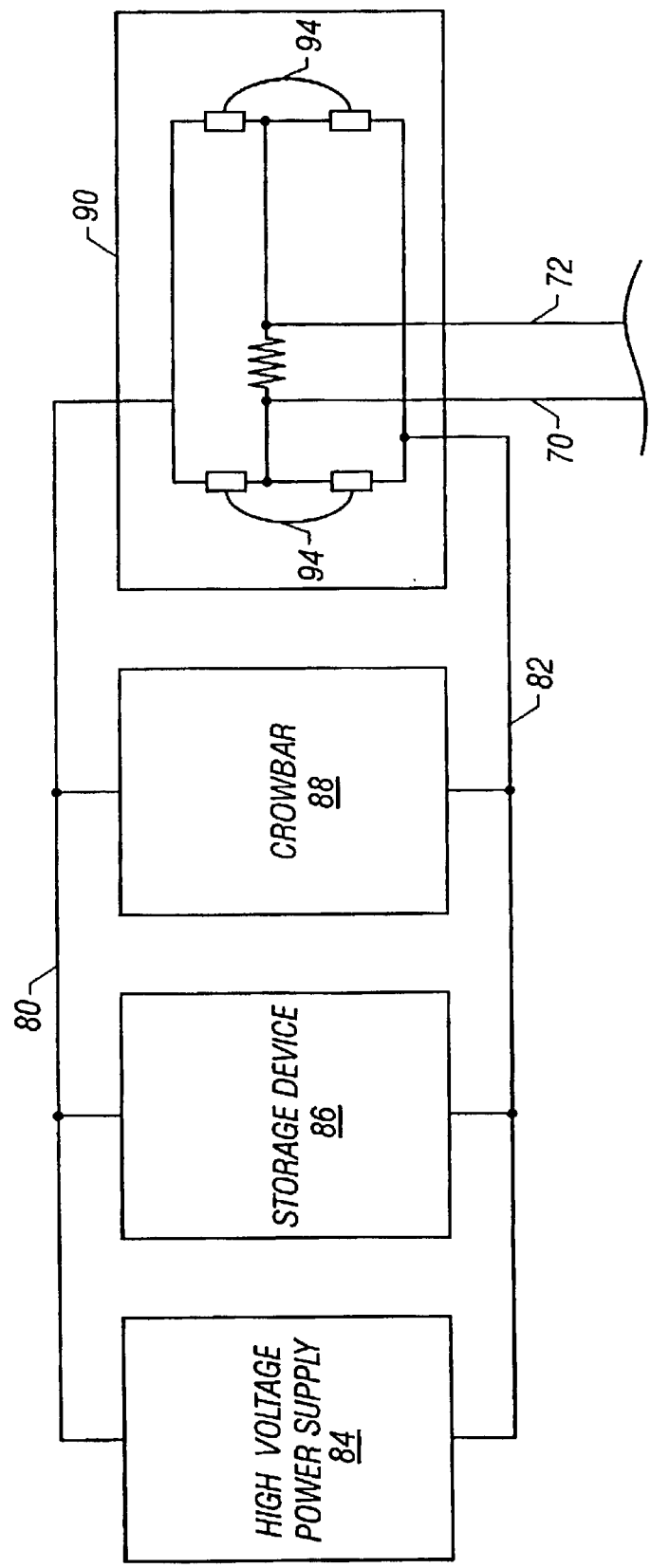
FIG. 9 illustrates an embodiment of signal generating electronics for generating bipolar electroporation signals. The signal generating electronics includes a single power source.

FIG. 9 illustrates an embodiment of signal producing electronics for producing therapeutic signals having a bipolar square waveform. The signal producing electronics include a first power line 80 and a second power line 82. An energy source 84, a storage device 86, a crowbar 88 and a polarity switching device 90 are connected to the first power line 80 and the second power line 82. The storage device 86 preferably applies a monopolar signal to the first power line 80 and the second power line 82 and must have enough capacity to deliver the therapeutic electrical signals to the electrodes 16. A suitable storage device 86 includes one or more capacitors. The energy source 84 can be any energy source 84 capable of charging the storage device 86 within the time requirements of the electroporation instrument 12. The controller 56 can use the crowbar 88 to short the storage device 86 in case a fault condition is detected. Hence, the controller 56 can use the crowbar 88 to prevent the energy within the storage device 86 from being discharged into a patient.

The polarity changing electronics include a plurality of switches 94 arranged in an H bridge. The switches are preferably MOSFET or IGBT switches. A first switch 94A and a second switch 94B are connected in series with the storage device 86. Similarly, a third switch 94C and a fourth switch 94D are connected in series with the storage device 86 and in parallel with the first switch 94A and the second switch 94B. A first connection line 96 connects the first switch 94A to the second switch 94B and a second connection line 98 connects the third switch 94C to the fourth switch 94D. A first bridge line 100 connects a resistor 102 to the first connection line 96. A second bridge line 104 connects the resistor 102 to the second connection line 98. The first output line 70 is connected to the first bridge line 100 and the second output line 72 is connected to the second bridge line 104.

Figure 10:
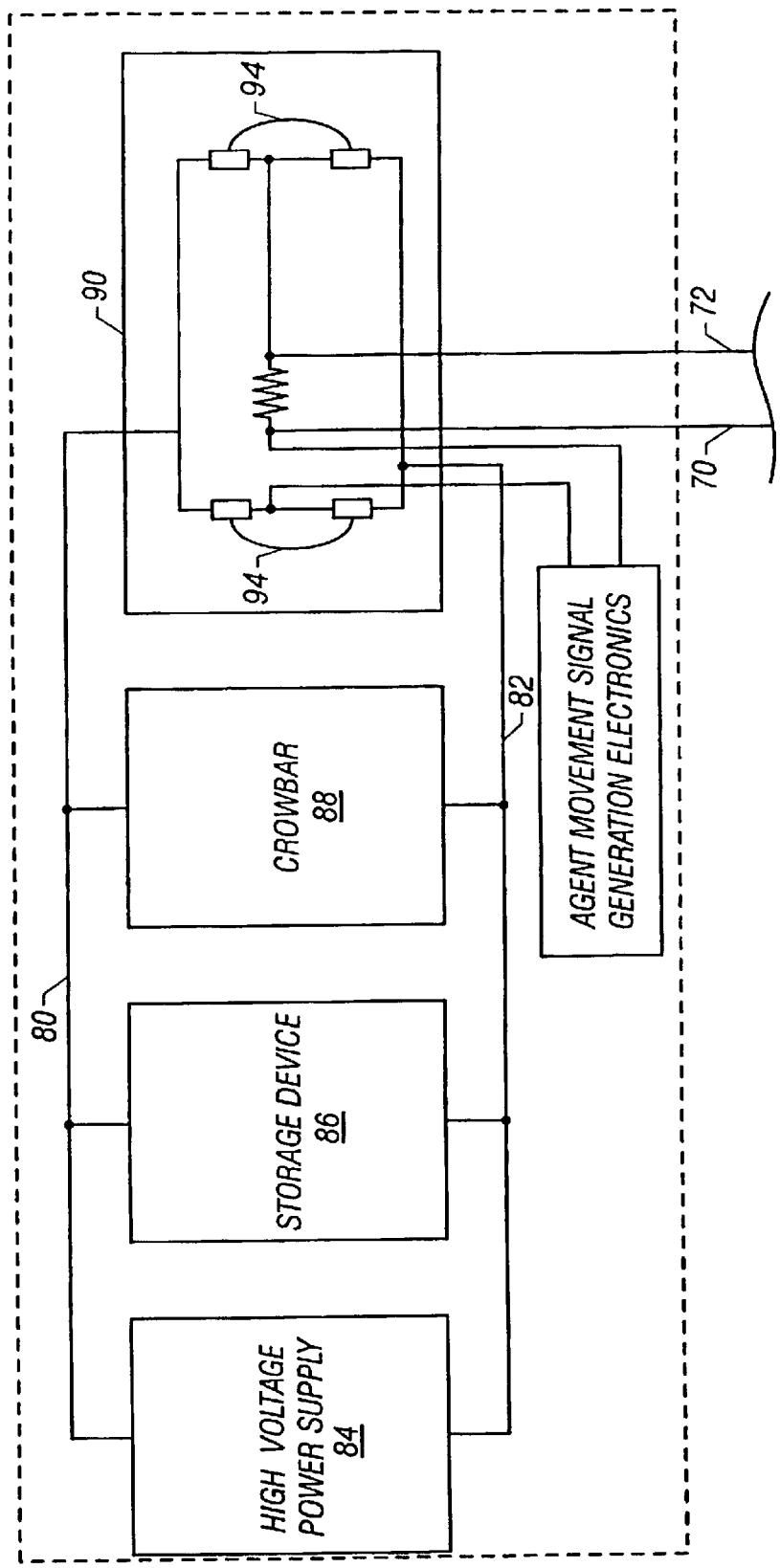
FIG. 10 illustrates signal generating electronics for generating electroporation signals and/or agent movement signals.

FIG. 10 illustrates the signal generating electronics 62 of FIG. 9 adapted to provide agent movement signals in addition to electroporation signals. Agent movement signal generating electronics 62 are tapped into the first bridge line 100 between the first output line 70 and the first connection line 96. The agent movement signal generating electronics add an agent movement signal to the bipolar signal created by the polarity switching electronics. For instance, when the agent movement signal is a DC signal, the agent movement signal adds a DC offset to the electroporation signals. The agent movement signal generating electronics can beactivated before, after or during the delivery of the bipolar signals. As a result, the therapeutic electrical signals can include an agent movement signal by itself, a bipolar signal by itself or a combination of both.

Suitable agent movement signals for use with the present invention include low voltage monopolar signals. As a result, the agent movement signal generating electronics can include a low voltage DC source such as a battery. Additionally, the agent movement signal generating electronics can include a switching system for selectively adding and removing the agent movement signal to the therapeutic electrical signal. The agent movement signals preferably have a potential of about 5 V-200 V and more preferably about 10 V-100 V. Additionally, the duration of the agent movement signals is preferably about 100 µs–10 seconds.

Figure 11A:
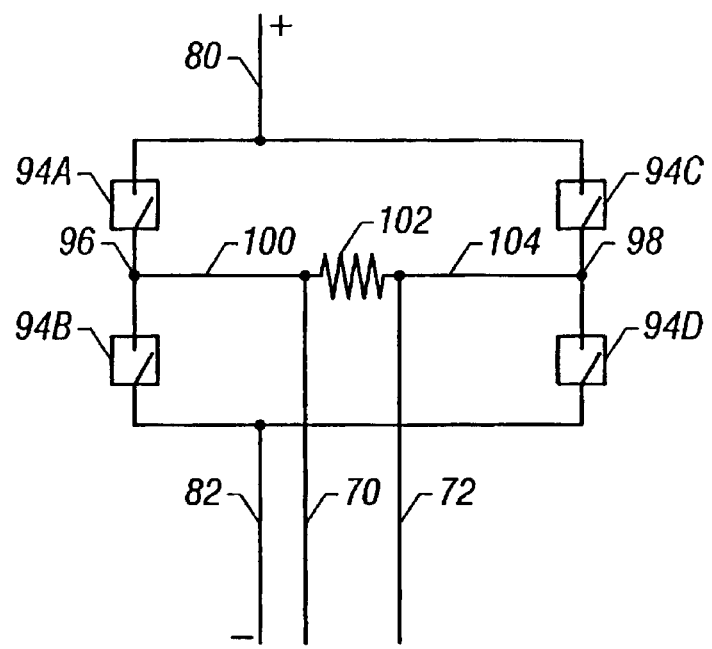
FIG. 11A illustrates polarity changing electronics in a standby configuration.

During operation of the electroporation instrument, the switches of the polarity changing electronics can occupy a variety of different configurations as illustrated in FIGS. 11A–11D. FIG. 11A illustrates a standby configuration where each of the switches are open. For purposes of illustration, the first power line 80 is illustrated as having a positive potential and the second power line 82 is illustrated with a negative potential. Since each of the switches are open, current does not flow and there is no potential on either the first output line 70 or the second output line 72.

Figure 11B:
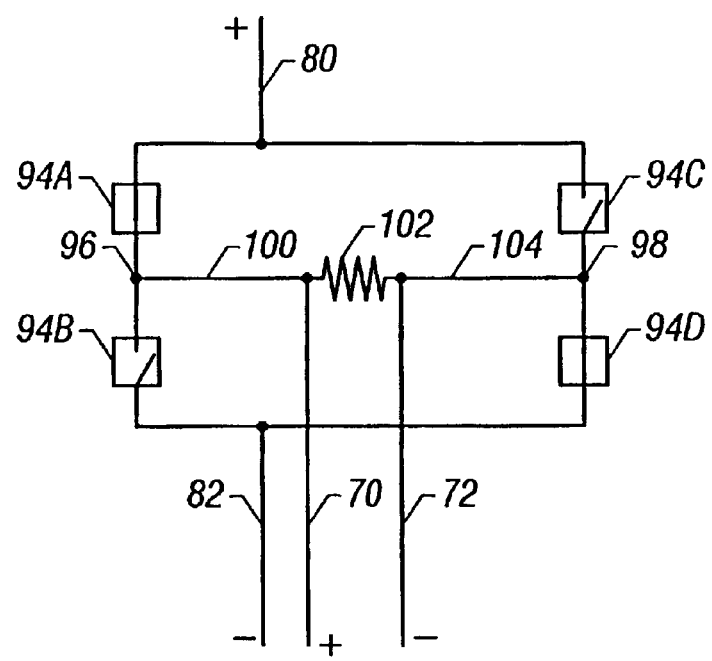
FIG. 11B illustrates polarity changing electronics in a first polarity configuration.

FIG. 11B illustrates a first polarity configuration for the switches. The first switch 94A and the fourth switch 94D are closed while the second switch 94B and the third switch 94C and open. Hence, the first power line 80 is connected to the first output line 70 and the second power line 82 is connected to the second output line 72. Accordingly, the positive potential of the first power line 80 is evident on the first output line 70 and the negative potential of the second power line 82 is evident on the second output line 72.

Figure 11C:
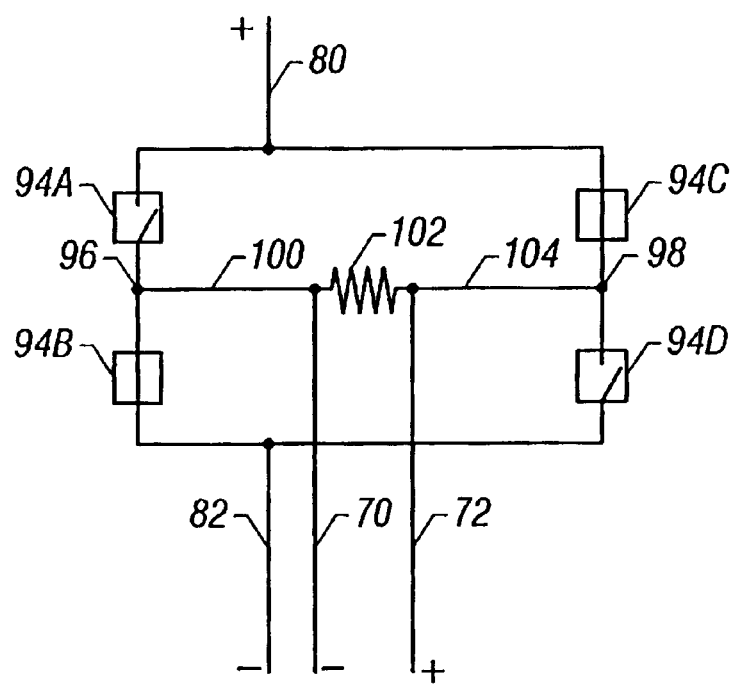
FIG. 11C illustrates polarity changing electronics in a second polarity configuration.

FIG. 11C illustrates a second polarity configuration for the switches. The first switch 94A and the fourth switch 94D are open while the second switch 94B and the third switch 94C and closed. Hence, the first power line 80 is connected to the second output line 72 and the second power line 82 is connected to the first output line 70. Accordingly, the positive potential of the first power line 80 is evident on the second output line 72 and the negative potential of the second power line 82 is evident on the first output line 70. As a result, the polarity of the first output line 70 and the second output line 72 is the opposite of what is illustrated in FIG. 11B.

Figure 11D:
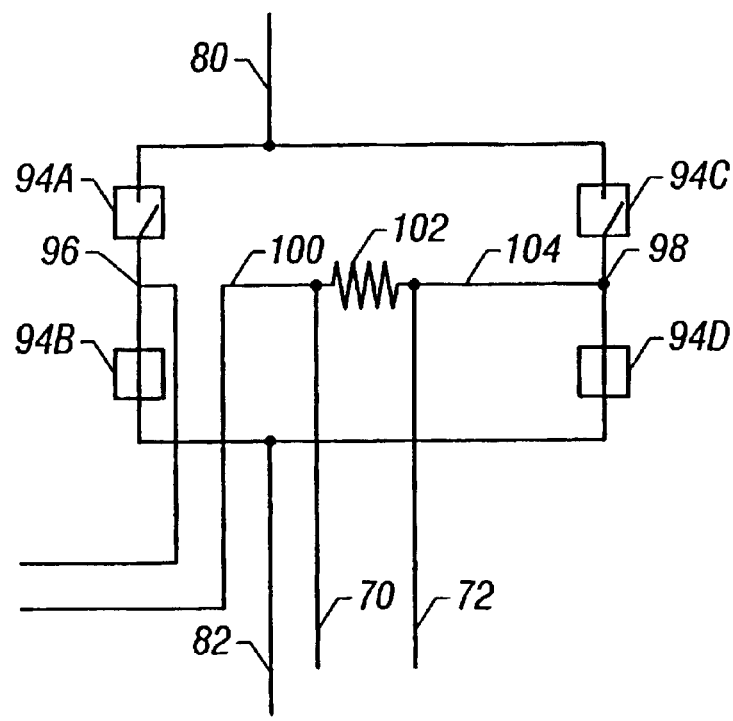
FIG. 11D illustrates polarity changing electronics in a configuration for providing agent movement signals in the absence of electroporation signals.

When the signal generating electronics 62 include agent movement signal generating electronics, the agent movement signal can be applied to the electrodes 16 without the electroporation signals by using the configuration illustrated in FIG. 11D. The second and fourth switches are closed to prevent the flow of the electroporation signals. However, the first and third switches are open to permit flow of agent movement signals. Hence, the agent movement signals are applied to the electrodes 16 without the electroporation signals. This switch configuration is employed when the agent movement signal is desired without the electroporation signal. For instance, this configuration can be employed between delivery of electroporation signals in order to encourage an agent to enter the pores opened by the electroporation signals.

During operation of the electroporation instrument 12, the switches are left in the standby configuration before and after delivery of the therapeutic electrical signals. To deliver a therapeutic electrical signal of a single pulse, the switches are transferred to either the first configuration polarity configuration or the second polarity configuration depending on the desired polarity. The switches a kept in this configuration for the desired pulse duration and then they are returned to the standby configuration.

To create a bipolar therapeutic electrical signal, the switches are alternated between the first polarity configuration and the second polarity configuration at the desired frequency. When an electroporation signal having a first polarity duration 46A which is different than a second polarity duration 46B is desired, the switches are held in the first configuration for the first polarity duration 46A and the second configuration for the second polarity duration 46B. Additionally, when an electroporation signal having a first polarity peak potential which is different than a second polarity peak potential is desired, the agent movement signal generating electronics can be selectively engaged in order to add additional potential to one or more portions of an electroporation signal.

The time delay needed to switch between switch configuration should be taken into account when creating electroporation signals having a desired waveform since this time delay can reduce the pulse duration at high frequencies. When MOSFET switches are employed, the time delay needed to change from one switch configuration to another switch configuration is on the order of tens of nanoseconds. As an alternative to alternating between configurations based on frequency, the switches can be held in each configuration for a time equal to the desired pulse length plus the time delay before moving to another switch configuration.

The signal generating electronics 62 illustrated in FIGS. 11A–11D create a bipolar waveform from a single power source. The use of a single power source provides advantages over signal generation electronics employing more than one power source. Specifically, since a monopolar signal is converted to a bipolar signal, the characteristics of the signal are the same regardless of the polarity. For instance, the potential of the signal in one polarity is the same as the potential of the signal when it has the opposite polarity. However, when a different power source is employed for each polarity, the potential of the signal at each polarity will be different due to the normal mechanical variations in potential produced by each power source.

Figure 12A:
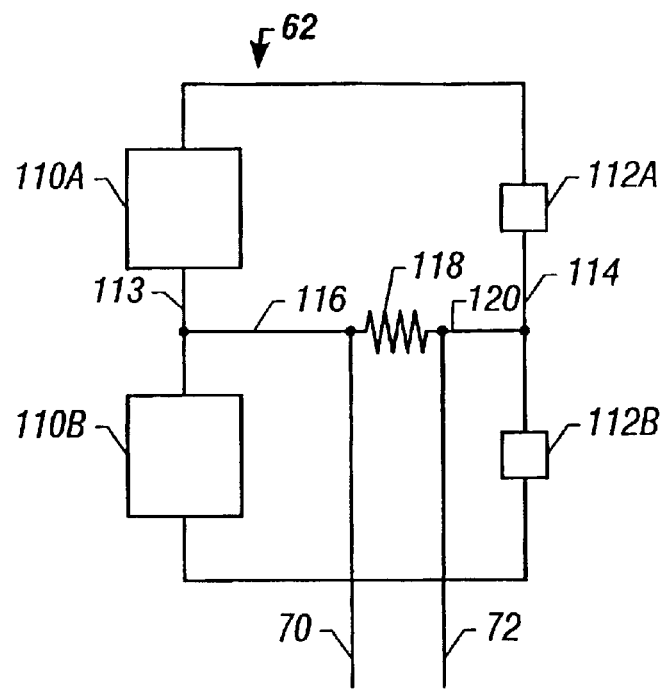
FIG. 12A illustrates an embodiment of signal generating electronics including a first power source and a second power source.

FIG. 12A illustrates signal generating electronics 62 employing a first power source 10A and a second power source 110B connected in series. The first power source 110A and the second power source 110B can include an energy source and a storage device as disclosed with respect to the signal generating electronics 62 illustrated in FIG. 9. The first power source 110A is connected in series with the second power source. A first switch 112A and a second switch 112B are connected in series between the first power source 110A and the second power source. The first switch 112A and the second switch 112B are preferably MOSFET or IGBT switches. A first connection line 113 connects the first power source 110A to the second power source. Similarly, a second connection line 114 connects the first switch 112A to the second switch 112B. A first bridge line 116 connects a resistor 118 to the first connection line 113. Additionally, a second bridge line 120 connects the resistor 118 to the second connection line 114. The first output line 70 is connected to the first bridge line 116 and a second output line 72 is connected to the second bridge line.

Figure 12B:
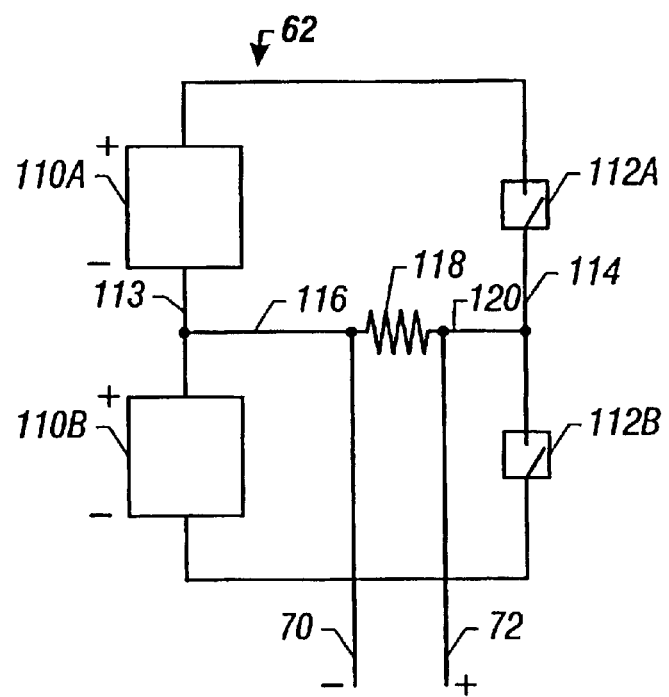
FIG. 12B illustrates the signal generating electronics of FIG. 12A in a first polarity configuration.
Figure 12C:
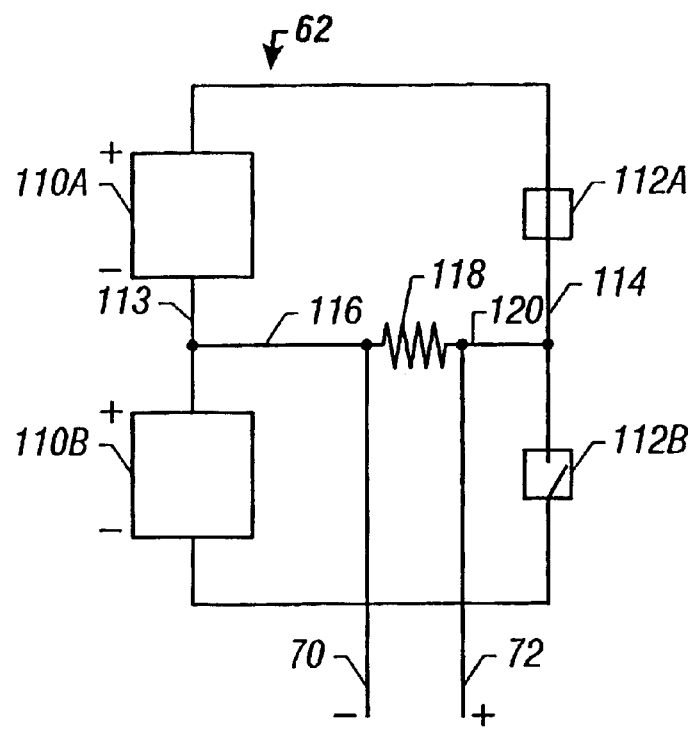
FIG. 12C illustrates the signal generating electronics of FIG. 12A in a second polarity configuration.
Figure 12D:
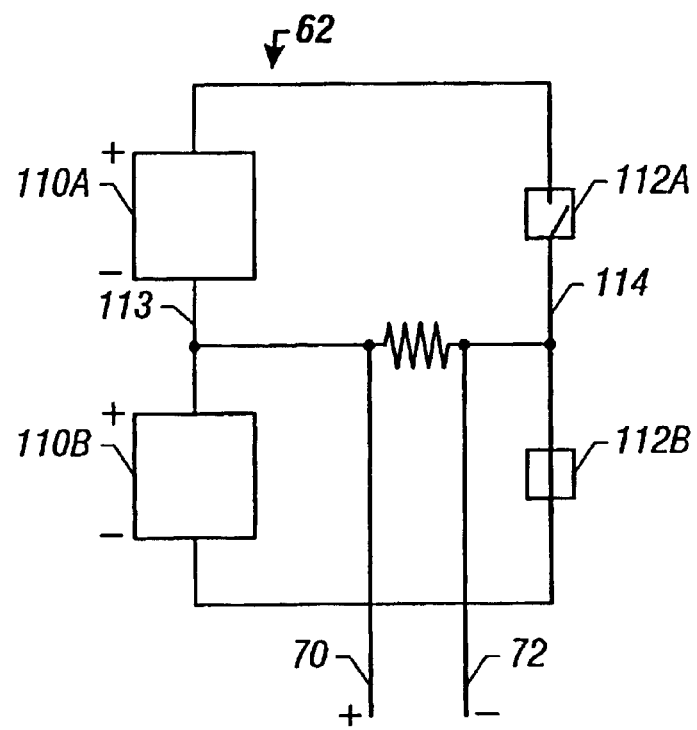

FIGS. 12B–12D illustrate a plurality of configurations which can be occupied by the switches. For the purposes of the following discussion, one end of each power source is labeled positive while the other end of each power source is labeled negative, however, the power sources can be connected in the opposite direction. FIG. 12B illustrates a standby configuration where each of the switches are open. Since each of the switches are open, current does not flow and there is no potential illustrated on either the first output line 70 or the second output line 72. The standby configuration can be employed before and after the delivery of the therapeutic signals.

FIG. 12C illustrates a first polarity configuration for the switches. The first switch 112A is closed while the second switch 112B is open. The open second switch 112B disrupts current flow from the second power source. The closed first switch 112A connects the positive terminal of the first power source 110A to the second output line 72. As a result, the positive potential of the first power source 110A is evident on the second output line 72 and the negative potential of the first power source 110A is evident on the first output line 70.

FIG. 12D illustrates a second polarity configuration for the switches. The first switch 112A is open while the second switch 112B is closed. The open first switch 112A disrupts current flow from the first power source. The closed second switch 112B connects the negative terminal of the first power source 110A to the second output line 72. As a result, the negative potential of the second power source 110B is evident on the second output line 72 and the positive potential of the second power source 110B is evident on the first output line 70. As a result, the polarity of the first output line 70 and the second output line 72 is the opposite of what is illustrated in FIG. 12C.

During operation of the electroporation instrument 12, the switches are left in the standby configuration before and after delivery of the therapeutic electrical signals. To deliver an electroporation signal of a single pulse, the switches are transferred to either the first configuration polarity configuration or the second polarity configuration depending on the desired polarity. The switches are kept in this configuration for the desired pulse duration and then they are returned to the standby configuration.

To create a bipolar therapeutic electrical signal, the polarity changing electronics are alternated between the first polarity configuration and the second polarity configuration at a frequency which provides the desired waveform. When an electroporation signal having a first polarity duration 46A which is different than a second polarity duration is desired, the switches are held in the first configuration for the first polarity duration and the second configuration for the second polarity duration. Additionally, when an electroporation signal having a first polarity peak potential which is different than a second polarity peak potential is desired, the power sources can have different voltages.

The time delay needed to switch between switch configuration should be taken into account when creating electroporation signals having a particular waveform since this time delay can reduce the pulse duration at high frequencies. When MOSFET switches are employed, the time delay needed to change from one switch configuration to another switch configuration is on the order of tens of nanoseconds. As an alternative to alternating between configurations based on frequency, the switches can be held in each configuration for a time equal to the desired pulse length plus the time delay before moving to another switch configuration.

Agent movement signal generating electronics can be tapped into the first bridge line 116 between the first output line 70 and the first connection line 113 similar to the illustration of FIG. 10. As a result, the signal generating electronics 62 illustrated in FIG. 12A can be adapted to produce agent movement signals in addition to the electroporation signals.

Although FIGS. 10–12D are directed toward signal generating electronics for development of electroporation signals having bipolar square waveforms, embodiments of the invention do not require these signal generating electronics. For instance, the electroporation instrument can include signal generating electronics for creation of electroporation, but not limited to, monopolar, triangular, circular, sinusoidal and exponential.

Figure 13:
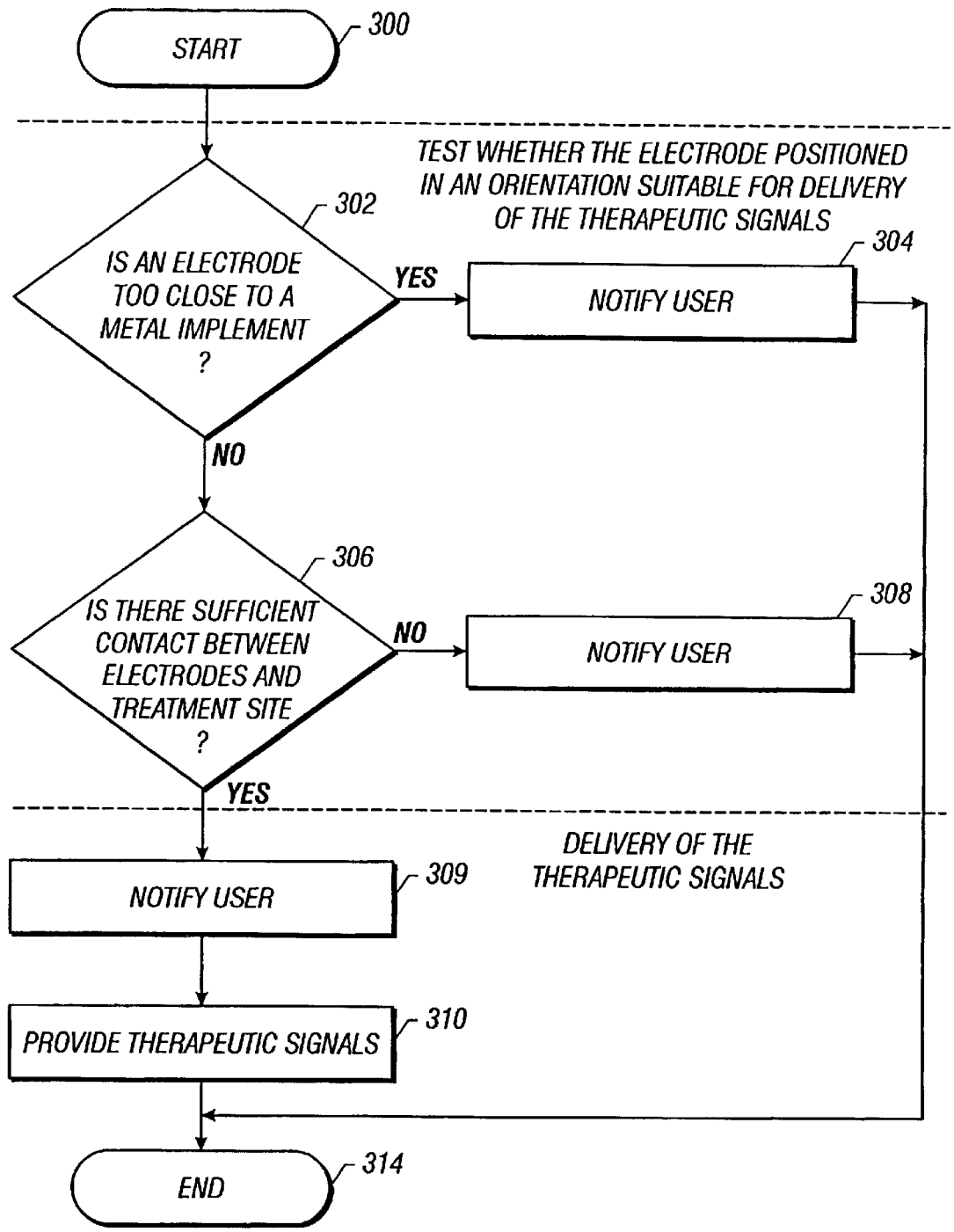
FIG. 13 is a process flow for a method of operating an electroporation instrument to provide an electroporation treatment.
Figure 16:
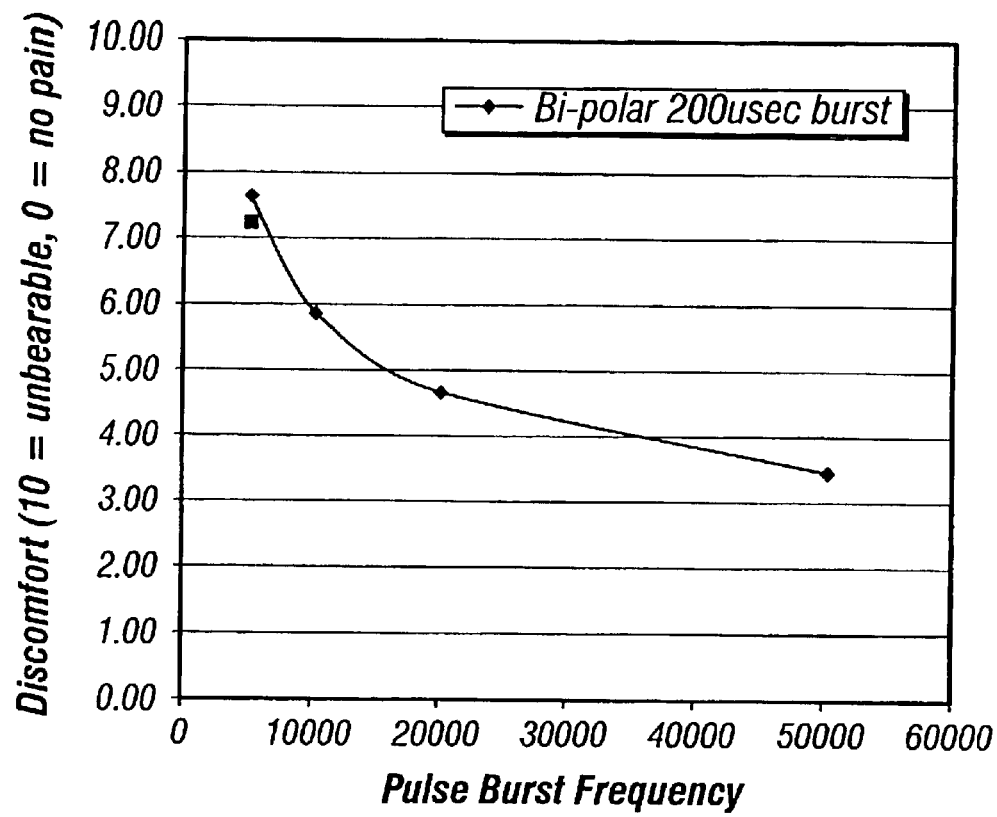
FIG. 16 illustrates experimental results illustrating that an increase in the frequency of the electroporation signals according to the present invention reduces the discomfort to the patient.

FIG. 13 illustrates a method of operating an electroporation instrument 12 according to the present invention. The method begins at start block 300 when an operator indicates to the electroporation instrument 12 that the electrodes 16 are in position for delivery of the therapeutic signals. At decision block 302 a test is performed to determine whether the electrodes 16 are positioned too close to a metal implement. FIG. 16 illustrates an example of a method for making this determination. If the determination is positive, the electroporation instrument operator is notified at process block 304. This notification can be provided to the operator by activating one with one or more of the user interfaces which is associated with the detected condition or which indicates the condition by means of a text or audible message. Additionally, the signal generation electronics can be temporarily disabled until an affirmative determination is made at determination block 302.

Figure 17:
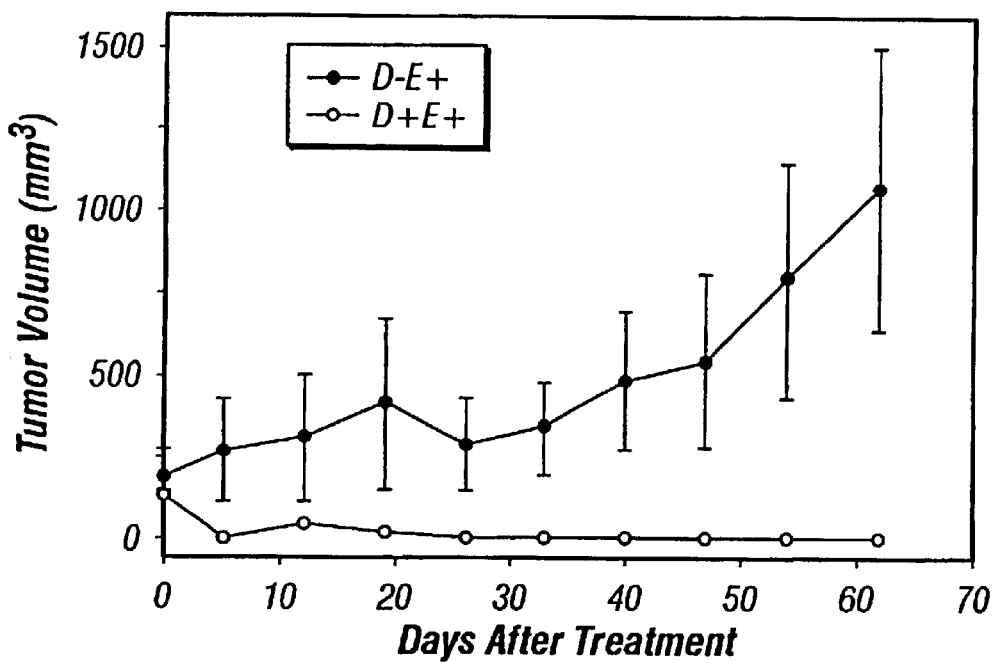
FIG. 17 illustrates the results of treating tumors in mice with electroporation therapy according to the present invention.

If the determination at decision block 302 is negative, a determination is made whether the degree of contact between the electrodes 16 and the treatment site 30 is sufficient for conduction of the therapeutic signals between the electrodes 16 and the treatment site 30 at decision block 306. An example of a method for making this determination is illustrated in FIG. 17. If the determination is negative, the user is notified at process block 308. This notification can be provided to the operator by activating one with one or more of the user interfaces which is associated with the detected condition or which indicates the condition by means of a text or audible message. If the determination at decision block 306 is positive, the user is notified at process block 309. The user can be notified with one of the user interfaces illustrated in FIG. 1. For instance, the user interface labeled "READY" can be lit to indicate that the electroporation instrument is ready to provide the therapeutic signals. Upon actuation of a remote controller 14 such as the foot pedal, the therapeutic signals are applied to the electrodes 16 at process bock 310. The method terminates at end block 312.

The method illustrated in FIG. 13 is for illustrative purposes only and other methods of operating an electroporation instrument are within the scope of the invention. For instance, as described above, the test for sufficiency of contact between an electrode and the treatment site can be performed before, during or after the application of the therapeutic electrical signals.

Figure 14:
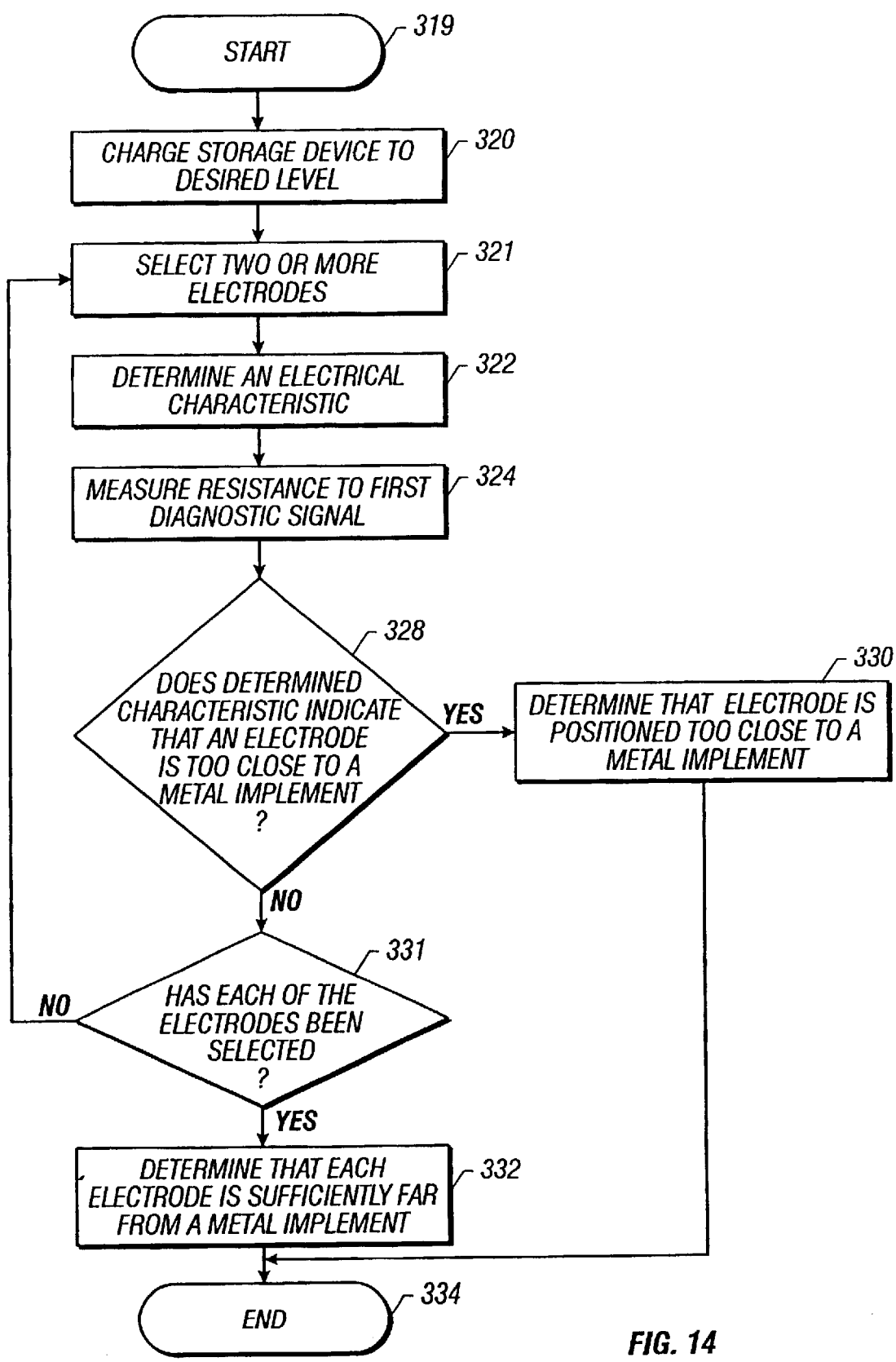
FIG. 14 is a process flow for a method of operating an electroporation instrument to test whether an electrode of the electroporation therapy apparatus is positioned too close to a metal implement to safely deliver the electroporation signals.

FIG. 14 illustrates a method of testing whether an electrode is positioned too close to a metal implement. The following description presumes that the electroporation instrument includes the signal generating electronics 62 disclosed in FIG. 9, however, the method can be easily adapted for use with other signal generating electronics 62. The method begins are process block 320 where the storage device 86 is charged to a level appropriate for delivering a first diagnostic signal to the electrodes 16. Since the first diagnostic signal preferably has a lower potential than the electroporation signals, the storage device 86 is preferably only partially charged. At process block 321 two or more of the electrodes 16 on the electroporation apparatus are selected. At process block 322, the first diagnostic signal is applied to the selected electrodes 16. The first diagnostic signal can be applied to the selected electrodes 16 by operating the relay device 60 to connect the first output line 70 and the second output line 72 to the selected electrodes 16. The polarity changing electronics are then changed from the standby configuration to either the first polarity configuration or the second polarity configuration for the desired duration of the first diagnostic signal.

At process block, 324, the first diagnostic signal is used to determine the value of an electrical characteristic which is a function of the displacement of an electrode from a metal implement. Suitable electrical characteristics include, but are not limited to, the resistance of a treatment site to the first diagnostic signal, the current of the first diagnostic signal through the treatment site and the power dissipated by the treatment site. At decision block 328, a determination is made whether the determined electrical characteristic indicates that an electrode is positioned too close to a metal implement. This determination can be made by comparing the value of the determined characteristic to one or more criteria. For instance, the electrical characteristic can be the resistance to the first diagnostic signal and a criterion can be a resistance threshold. The resistance threshold can be selected such that when the resistance is greater than the resistance threshold, the therapeutic signals can be safely applied, i.e. there is a low danger of arcing between an electrode and a metal implement. Hence, when the resistance is less than the resistance threshold, the determination is positive. When the resistance is greater than the resistance threshold, the determination is negative.

If the determination at decision block 328 is positive, an electrode is determined to be too close to a metal implement at process block 330. If the determination at decision block 328 is negative, a determination is made whether each of the electrodes 16 has been selected at process block 331. If the determination is negative, the method returns to process block 321. If the determination is positive, each electrode is determined to be sufficiently far away from metal implements at process block 332. The method ends at end block 334.

Figure 15:
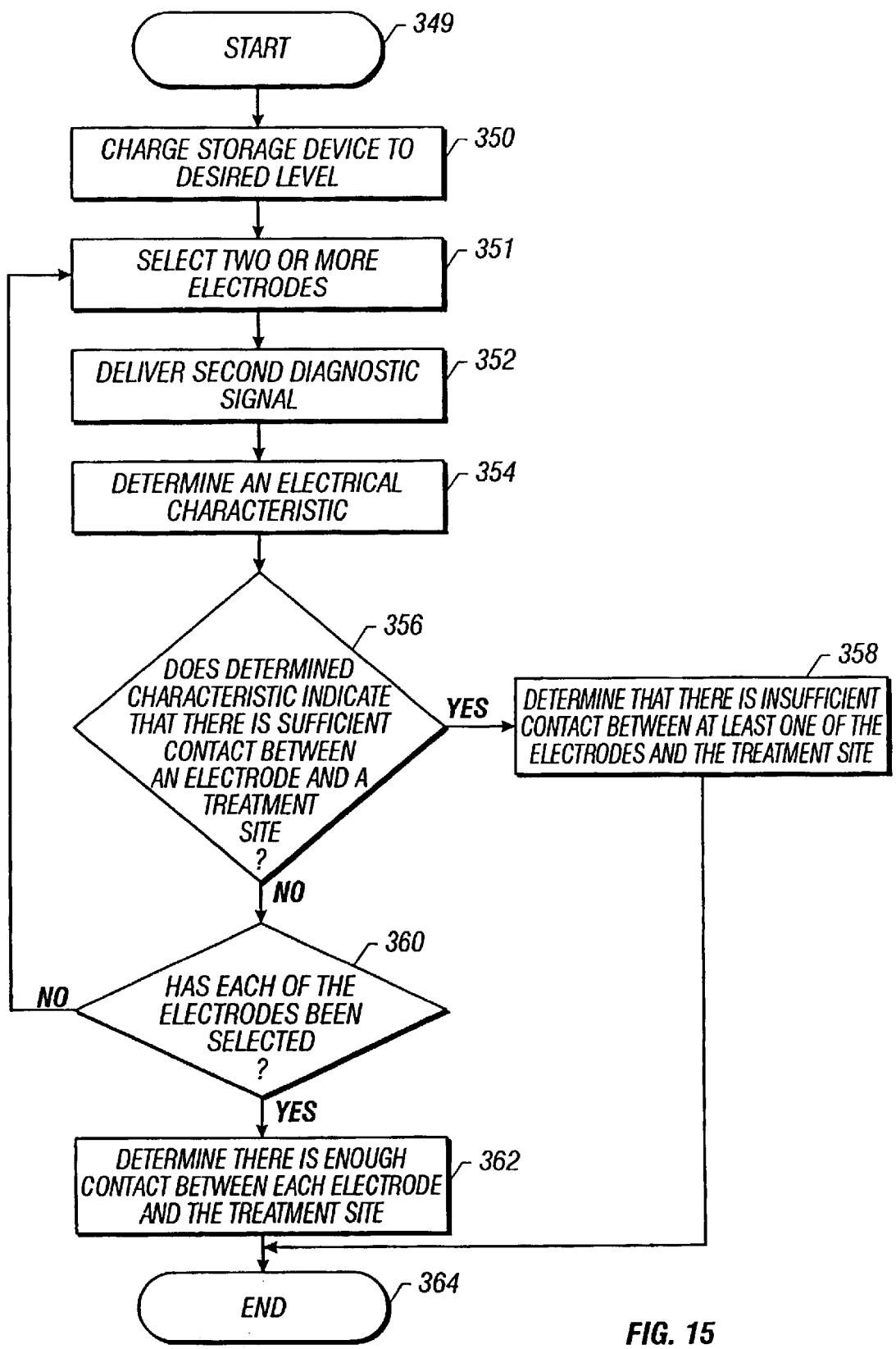
FIG. 15 is a process flow for a method of operating an electroporation instrument to test whether there is sufficient contact between each electrode and the treatment site for the therapeutic electrical signals to be conducted from the electrodes to the treatment site.

FIG. 15 illustrates a method of testing whether there is sufficient contact between each electrode and the treatment site 30 for the therapeutic electrical signals to be conducted from the electrodes 16 to the treatment site 30. The following description presumes that the electroporation instrument includes the signal generating electronics 62 disclosed in FIG. 9, however, the method can be easily adapted for use with other signal generating electronics 62. The method begins are process block 349. At process block 350, the storage device 86 is charged to a level appropriate for delivering a second diagnostic signal to the electrodes 16. The second diagnostic signal preferably has a higher potential than the first diagnostic signal. As a result, the storage device 86 can be charged beyond the level used to provide the first diagnostic signal at process block 320.

At process block 352, the second diagnostic signal is applied to the selected electrodes 16. The second diagnostic signal can be applied to the selected electrodes 16 by operating the relay device 60 to connect the first output line 70 and the second output line 72 to the selected electrodes 16. The polarity changing electronics are then changed from the standby configuration to either the first polarity configuration or the second polarity configuration for the desired duration of the second diagnostic signal.

At process block, 354, the second diagnostic signal is used to determine the value of an electrical characteristic which is a function of the degree of contact between an electrode and a treatment site. Suitable electrical characteristics include, but are not limited to, the resistance of a treatment site to the second diagnostic signal, the current of the second diagnostic signal through the treatment site and the power dissipated by the treatment site. At decision block 328, a determination is made whether the determined electrical characteristic indicates that the degree of contact between an electrode and the treatment site is sufficient to conduct the therapeutic signals from the electrode to the treatment site. This determination can be made by comparing the value of the determined characteristic to one or more criteria. For instance, the electrical characteristic can be the current of the second diagnostic signal and a criterion can be a current threshold. The current threshold can be selected such that when the current is less than the current threshold, there is enough contact between an electrode and the treatment site to properly conduct the therapeutic signals between the electrode and the treatment site. Hence, when the current is less than the current threshold, the determination is negative. When the current is greater than the current threshold, the determination is positive.

If the determination is negative, at least one electrode is determined to be in insufficient contact with the treatment site 30 at process block 358. If the determination at decision block 356 is positive, a determination is made whether each of the electrodes 16 has been selected at process block 360. If the determination is negative, the method returns to process block 351. If the determination is positive, each electrode is determined to be in sufficient contact with the treatment site 30 for the therapeutic signals to be conducted between the electrodes 16 and the treatment site 30 at process block 362. Although current is used in the description of the above method, the method can be performed using any electrical characteristic which is a function of the degree of contact between an electrode and the treatment site 30.

In one embodiment of the invention, the first diagnostic signal and the second diagnostic signal are the same signal. Hence, the method of both FIG. 14 and FIG. 15 can be performed using a single diagnostic signal. In another embodiment of the method, one or more therapeutic electrical signals serves as the second diagnostic signal. Since delivering the therapeutic electrical signals while there is insufficient contact between an electrode and the treatment site does not cause unusual discomfort or danger to the patient, the therapeutic electrical signals can be delivered and can serve as the second diagnostic signal. In this embodiment, an operator is informed of the insufficient contact during or after the delivery of the therapeutic electrical signals. Further, the methods discussed with respect to FIG. 14 and FIG. 15 are not limited to in vivo applications.

The methods, apparatuses, systems and instruments described above can be used in a method for delivery of an agent to a cell. The method includes positioning one or more electrodes such that an electrical signal passed between the one or more electrodes passes through the cell and passing an electrical signal between at least two of the one or more electrodes. In one embodiment, the electrical signal includes an electroporation signal. In another embodiment, the electrical signal includes an electroporation signal and/or an agent movement signal. One embodiment of the method also includes introducing the agent into the proximity of the two or more electrodes.

The electroporation signals preferably have a frequency greater than about 10 kHz, more preferably at least about 40 kHz, even more preferably at least about 100 kHz and most preferably at least about 500 kHz. In one embodiment, the frequency is less than about 10 MHz, in another embodiment, the frequency is about 40 kHz-1 MHz and in yet another embodiment the frequency is about 100 kHz-500 kHz and in still another embodiment the frequency is greater than about 200 kHz and at most about 500 kHz.

Therapeutic electrical signals according to the present invention preferably have a pulse duration of less than about 50 μs, more preferably have a pulse duration of less than about 12.5 μs and most preferably a pulse duration of less than about 5 μs. In one embodiment of the invention, the pulse duration is about 80 ns–50 μs and in another embodiment of the invention the pulse duration is about 2 μs–50 μs.

Passing the electrical signals preferably includes creating an energy field of at least about 25 V/cm between at least two of the electrodes 16 and more preferably at least about 100 V/cm between at least two of the electrodes 16. In one embodiment of the method, passing the electrical signals preferably includes creating an energy field of about 100 V/cm–10 kV/cm, in another about 1 kV/cm-3 kV/cm and in another about 1 kV/cm-2 kV/cm.

As the electric field increases, the total electroporation signal duration can be decreased in order to prevent excessive amounts of energy from being delivered to the treatment site 30. The total electroporation signal duration is preferably less than about 10 seconds, more preferably about 30 μs–10 seconds, even more preferably about 30 μs–1 ms and most preferably about 50 μs–400 ms.

To achieve these electric fields within treatment sites 30 including tumors 34 having typical dimensions, the electroporation signal preferably has a potential of less than about 10 kV, more preferably at least about 500 V and most preferably at least about 10 V. In one embodiment of the invention, the electroporation signal has a potential of about 500 V-10 kV and in another embodiment the electroporation signal has a potential of about 1 kV-5 kV and in yet another embodiment the electroporation signal has a potential of about 1 kV-3 kV.

As described above, electroporation therapy includes introduction of one or more agents to a subject and delivery of therapeutic electrical signals to the treatment site 30. The one or more agents can be introduced before, after or during the delivery of the therapeutic electrical signals. Suitable agents for use with the invention include, but are not limited to, drugs (e.g., chemotherapeutic agents), small molecules, nucleic acids (e.g., polynucleotides), peptides, polypeptides and peptidomimetics, including antibodies. The term polynucleotides include DNA, cDNA, RNA sequences and complementary sequences thereto.

The electroporation signals according to the method can have a monopolar waveform but preferably have a bipolar waveform. Suitable waveforms include, but are not limited to, square, triangular, circular and exponential. As described above, the waveform for in vivo delivery is preferably a bipolar square waveform.

Drugs contemplated for use in the methods, apparatuses and instruments of the invention are typically chemotherapeutic agents having an antitumor or cytotoxic effect. Such drugs or agents include bleomycin, neocarcinostatin, suramin, doxorubicin, carboplatin, taxol, mitomycin C and cisplatin. Other chemo-therapeutic agents will be known to those of skill in the art (see for example The Merck Index). In addition, agents that are A membrane≡acting-agents are also included in the method of the invention. These agents may also be agents as listed above, or alternatively, agents which act primarily by damaging the cell membrane. Examples of membrane-acting agents include N-alkylmelamide and para-chloro mercury benzoate. The chemical composition of the agents will dictate the most appropriate time to administer the agent in relation to the administration of the electric pulse. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug within the field. Further, such drugs as bleomycin, which have a very negative log P, (P being the partition coefficient between octanol and water), are very large in size (MW=1400), and are hydrophilic, thereby associating closely with the lipid membrane, diffuse very slowly into a tumor cell and are typically administered prior to or substantially simultaneous with the electric pulse. In addition, certain agents may require modification in order to allow more efficient entry into the cell. For example, an agent such as taxol can be modified to increase solubility in water which would allow more efficient entry into the cell. Electroporation facilitates entry of bleomycin or other similar drugs into the tumor cell by creating pores in the cell membrane.

It may be desirable to modulate the expression of a gene in a cell by the introduction of a molecule by the method of the invention. The term Amodulate≡envisions the suppression of expression of a gene when it is over-expressed, or augmentation of expression when it is under-expressed. Where a cell proliferative disorder is associated with the expression of a gene, nucleic acid sequences that interfere with the gene=s expression at the transnational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and Ahammerhead=-type. Tetrahymena-type ribozymes recognize sequences which are four bases in length, while Ahammerhead≡-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The invention also provides gene therapy for the treatment of cell proliferative or immunologic disorders mediated by a particular gene or absence thereof. Such therapy would achieve its therapeutic effect by introduction of a specific sense or antisense polynucleotide into cells having the disorder. Delivery of polynucleotides can be achieved using a recombinant expression vector such as a chimeric virus, or the polynucleotide can be delivered as Anaked≡DNA for example.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated.

Therapeutic peptides or polypeptides may also be included in the therapeutic method of the invention. For example, immunomodulatory agents and other biological response modifiers can be administered for incorporation by a cell. The term Abiological response modifiers≡is meant to encompass substances which are involved in modifying the immune response. Examples of immune response modifiers include such compounds as lymphokines. Lymphokines include tumor necrosis factor, interleukins 1, 2, and 3, lymphotoxin, macrophage activating factor, migration inhibition factor, colony stimulating factor, and alpha-interferon, beta-interferon, and gamma-interferon and their subtypes.

Also included are polynucleotides which encode metabolic enzymes and proteins, including antiangiogenesis compounds, e.g., Factor VIII or Factor IX. The macromolecule of the invention also includes antibody molecules. The term Aantibody≡as used herein is meant to include intact molecules as well as fragments thereof, such as Fab and F(ab=)$_2$.

Administration of a drug, polynucleotide or polypeptide, in the method of the invention can be, for example, parenterally by injection, rapid infusion, nasopha-ryngeal absorption, dermal absorption, and orally. Additionally, administration can be systemic or local. For instance, the delivery can be intratumorally, intraarterially, intramuscularly, transdermally, intradermally and intravenously. In the case of a tumor 34, for example, a chemotherapeutic or other agent can be administered systemically or directly injected into the tumor 34. When a drug, for example, is administered directly into the tumor 34, it is advantageous to inject the drug in a Afanning≡manner. The term Afanning≡refers to administering the drug by changing the direction of the needle as the drug is being injected or by multiple injections in multiple directions like opening up of a hand fan, rather than as a bolus, in order to provide a greater distribution of drug throughout the tumor 34. As compared with a volume that is typically used in the art, it is desirable to increase the volume of the drug-containing solution, when the drug is administered (e.g., injected) intratumorally, in order to insure adequate distribution of the drug throughout the tumor 34. For example, in the EXAMPLES using mice herein, one of skill in the art typically injects about 50 Φl of drug-containing solution, however, the results are greatly improved by increasing the volume to about 150 Φl. In the human clinical studies, about 20 ml was injected to ensure adequate perfusion of the tumor 34. Preferably, the injection should be done very slowly all around the base and by fanning. Although the interstitial pressure is very high at the center of the tumor 34, it is also a region where very often the tumor 34 is necrotic.

Preferably, the agent is administered substantially contemporaneously with the electroporation treatment. The term Asubstantially contemporaneously≡means that the agent and the electroporation treatment are administered reasonably close together with respect to time. The administration of the agent can at any interval, depending upon such factors, for example, as the nature of the tumor 34, the condition of the patient, the size and chemical characteristics of the agent.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Besides the inert diluents, such compositions can also include adjuvants, wetting agents, emulsifying and suspending agents. Further, vasoconstrictor agents can be used to keep the therapeutic agent localized prior to pulsing.

Any cell can be treated by the methods, apparatuses and instruments of the invention. The illustrative examples provided herein demonstrate the use of the method of the invention for the treatment of tumor cells, e.g., pancreas, lung, head and neck, cutaneous and subcutaneous cancers. Other cell proliferative disorders, such as warts, are amenable to treatment by the electroporation method of the invention. The term Acell proliferative disorder≡denotes malignant as well as non-malignant cell populations which often appear to differ from the surrounding tissue both morphologically and genotypically. Malignant cells (i.e., tumors 34 or cancer) develop as a result of a multi-step process. The methods of the invention are useful in treating malignancies or other disorders of the various tissues such as cardiac tissue, arterial tissue and venous tissue. The methods of the invention are also useful in treating malignancies and or other disorders of the various organ systems including, but not limited to, cells in the pancreas, head and neck (e.g., larynx, nasopharynx, oropharynx, hypopharynx, lip, throat,) and lung, and also including cells of heart, kidney, muscle, breast, colon, prostate, thymus, skin, testis, cervix, vagina, uterus and ovary. Further, malignancies of the skin, such as basal cell carcinoma or melanoma can also be treated by the therapeutic method of the invention as can pre cancerous lesions, pre cancerous skin lesions. Preferably the subject is human, however, it should be understood that the invention is also useful for veterinary uses in non-human animals or mammals.

The advantages offered by electroporation for skin and muscle-directed gene therapy and vaccination include: (1) elimination of the risk of generating novel disease-causing agents; (2) delivery of DNA molecules much larger than can be packaged into a virus; (3) no immune responses or toxic side effects by non-DNA material, e.g., viral proteins or cationic lipids; (4) DNA enters the cell through a non-endosomal pathway, diminishing the rate of DNA degradation; and (5) the method is simple, highly reproducible and cost-effective.

In accordance with the present invention, there are provided in vivo methods for introducing a therapeutic agent into skin or muscle cells of a subject. The method includes applying a pulsed electric field to skin or muscle cells substantially contemporaneously with the application of an antigen or antigen-encoding nucleic acid molecule such that the antigen or antigen-encoding nucleic acid molecule is introduced into the cell. In addition, an adjuvant or a CpG-containing oligonucleotide can be substantially contemporaneously administered with the antigen or antigen-encoding nucleic acid molecule. The term "substantially contemporaneously" means that the CpG-containing oligonucleotide and an antigen or antigen-encoding nucleic acid molecule and the electroporation treatment are administered reasonably close together with respect to time. The administration of the adjuvant or CpG-containing oligonucleotide and an antigen or antigen-encoding nucleic acid molecule can occur at any interval, depending upon such factors, for example, as the nature of the tissue to be electroporated, the condition of the patient, the size and chemical characteristics of the antigen and half-life of the antigen or antigen-encoding nucleic acid molecule.

Therefore, in accordance with another embodiment, the present invention provides a method for the introduction of nucleic acid and/or antigens into the cells of the skin and/or muscle, preferably human, by contacting the skin with nucleic acid and applying an electrical pulse to the targeted region. The electrical pulse is of sufficient voltage and duration to cause electroporation so that the antigen or antigen-encoding nucleic acid molecule can penetrate into the cells of the skin and/or muscle and nucleic acid molecule can be expressed as a transgenic molecule. The biological expression of the nucleic acid component results in the transcription and translation of the delivered gene so that the targeted cells synthesize gene product de novo. Therapeutic applications include, for example, the augmentation of missing or under-expressed genes; the expression of genes that have a therapeutic value (e.g., inhibiting the action of harmful gene products by expressing a receptor to bind the product of an over-expressed gene); the expression of genes, the product of which elicits a desired immune response; delivery of a DNA vaccine in conjunction with a CpG-containing oligonucleotide; and the like.

As will be understood by those of skill in the art, efficient expression of a nucleic acid encoding a polypeptide generally requires that the nucleic acid sequence be operably associated with a regulatory sequence. Regulatory sequences contemplated for use in the practice of the present invention include promoters, enhancers, and the like. As those of skill in the art will also appreciate, even when a promoter sequence is operably associated with the therapeutic nucleic acid, expression may be further augmented by operably associating an enhancer element or the like.

Promoters contemplated for use in DNA vaccines of the present invention include the CMV, RSV LTR, MPSV LTR, SV40, the group of keratin specific promoters (e.g., the keratin and involucrin group of promoters. Presently, it is preferred that the promoters employed in the practice of the present invention are specifically active in skin cells. The transcriptional promoters of a number of genes expressed in the epidermis have been characterized. Furthermore, such promoters tend to restrict expression to either the basal compartment or the suprabasal compartment. Keratin 14, for example, is expressed by basal keratinocytes, whereas involucrin is expressed by suprabasal keratinocytes. In addition, the keratin 14 and involucrin genes are highly expressed in keratinocytes, thus use of their promoters to drive transgene transcription yields not only target specificity, but also high levels of expression. The promoters for both genes have been successfully used to direct compartment-specific expression to the epidermis of transgenic mice.

In one aspect of the present invention, the molecules to be introduced are topically applied. It should be understood that the electroporation of tissue can be performed in vitro, in vivo, or ex vivo. Electroporation can also be performed utilizing single cells, e.g., single cell suspensions or in vitro or ex vivo in cell culture.

Nucleic acids contemplated for use in the practice of the present invention include naked DNA, naked RNA, naked plasmid DNA, either supercoiled or linear, and encapsulated DNA or RNA (e.g., in liposomes, microspheres, or the like). As will be understood by those of skill in the art, particles mixed with plasmid so as to "condense" the DNA molecule may also be employed. Delivery of polynucleotides can be achieved using a recombinant expression vector such as a chimeric virus, or the polynucleotide can be delivered as "naked" DNA for example.

The polynucleotide sequences of the invention are DNA or RNA sequences having a therapeutic (e.g., immune response inducing or augmenting) effect after being taken up by a cell. Nucleic acids contemplated for use in the practice of the present invention can be double stranded DNA (e.g., plasmid, cosmid, phage, viral, YACS, BACS, other artificial chromosomes, and the like), single stranded DNA or RNA. The nucleic acids may be uncomplexed (i.e., "naked") or complexed (e.g., with chemical agents such as lipids (e.g., cationic), dendrimers, or other polyplexes that facilitate DNA penetration into tissues and through cell membranes, and the like). The DNA may also be encapsulated or formulated with protein complexes.

As used herein, "polypeptide" is understood to be any translation product of a polynucleotide regardless of size, and whether glycosylated or not. Therapeutic polypeptides contemplated for use in the practice of the present invention include, as a primary example, those polypeptides that can induce an immune response in a subject.

In accordance with another embodiment of the present invention, there are provided methods for inducing or augmenting an immune response in a subject. Invention methods of this embodiment comprise applying a pulsed electric field to skin or muscle cells of the subject substantially contemporaneously with the application of antigen or antigen-encoding nucleic acid molecules to the skin or muscle cells, such that the antigen or antigen-encoding nucleic acid molecules is introduced into the skin or muscle cells thereby inducing or augmenting in the subject an immune response. As used herein, "antigen or antigen-encoding nucleic acid molecules" means any agent, which upon introduction into the skin or muscle cells of a subject, results in an immune response, whether the response be a cellular response, a humoral response, or a combination of both. Immune response-inducing agents contemplated for use in the practice of the present invention include expressible nucleic acids and polypeptides.

Expressible DNA and mRNA can be delivered to cells to form therein a polypeptide translation product. If the nucleic acids are operatively associated with the proper regulatory sequences, enhanced synthesis of the encoded protein is achievable. DNA or RNA encoded polypeptides contemplated for use in the practice of the present invention include immunizing polypeptides, pathogen-derived proteins, blood coagulation factors, peptide hormones, and the like. Peptide hormones include, for example, calcitonin (CT), parathyroid hormone (PTH), erythropoietin (Epo), insulin, cytokines, growth hormone, growth factors, and the like). Lymphokines contemplated for use in the practice of the present invention include tumor necrosis factor, interleukins 1, 2, and 3, lymphotoxin, macrophage activating factor, migration inhibition factor, colony stimulating factor, alpha-interferon, beta-interferon, gamma-interferon and subtypes thereof.

When the DNA or mRNA delivered to the cells codes for an immunizing peptide, invention methods can be applied to achieve improved and more effective immunity against infectious agents, including bacteria, intracellular viruses, tumor cells, and the like. Therapeutic polynucleotides provided by the invention can also code for immunity-conferring polypeptides, which can act as endogenous immunogens (i.e., antigen-containing polypeptides) to provoke a humoral immune response, a cellular immune response-inducing agent response, or both. Methods for inducing such responses and targeting specific cells for specific responses are described, for example, in U.S. Pat. No. 5,589,466. The polynucleotides employed in accordance with the present invention can also code for an antibody. In this regard, the term "antibody" encompasses whole immunoglobulin of any class, chimeric antibodies and hybrid antibodies with dual or multiple antigen or epitope specificities, and fragments, such as $F(ab)_2$, Fab', Fab, and the like, including hybrid fragments thereof. Also included within the meaning of "antibody" are conjugates of such fragments, and so-called antigen binding proteins (single chain antibodies) as described, for example, in U.S. Pat. No. 4,704,692, hereby incorporated by reference herein in its entirety.

Thus, an isolated polynucleotide coding for variable regions of an antibody can be introduced, in accordance with the present invention, to enable the treated subject to produce antibody in situ. For illustrative methodology relating to obtaining antibody-encoding polynucleotides, see Ward et al. *Nature,* 341:544–546 (1989); Gillies et al., *Biotechnol.* 7:799–804 (1989). The antibody in turn exerts a therapeutic effect, for example, by binding a surface antigen associated with a pathogen. Alternatively, the encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby ameliorating or preventing pathological conditions associated with an immune response, (e.g., in the context of an autoimmune disease such as lupus and the like).

It is presently preferred that polynucleotide sequences used in the practice of the present invention code for therapeutic or immunogenic polypeptides. These polynucleotide sequences may be used in association with other polynucleotide sequences coding for regulatory proteins that control the expression of the therapeutic or immunogenic polypeptides. The regulatory protein(s) so employed can act in any number of regulatory manners known to those of skill in the art, such as by binding to DNA so as to regulate its transcription, by binding to messenger RNA to increase or decrease its stability or translation efficiency, and the like.

The polynucleotide material delivered to the cells in vivo can take any number of forms, and the present invention is not limited to any particular polynucleotide coding for any particular polypeptide. Plasmids containing genes coding for a large number of physiologically active peptides and antigens or immunogens are contemplated for use in the practice of the present invention and can be readily obtained by those of skill in the art.

Various viral vectors can also be utilized in the practice of the present invention and include adenovirus, herpes virus, vaccinia, RNA virus, and the like. It is presently preferred that the virus be an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV), or the like can be utilized. A number of additional retroviral vectors can incorporate multiple genes. All of these vectors can transfer or incorporate a gene for a selectable marker so that transduced cells can be identified and generated.

Therapeutic peptides or polypeptides may also be included in the therapeutic method of the invention. For example, immunomodulatory agents and other biological response modifiers can be administered for incorporation by a cell. As used herein, the term "biological response modifiers" encompasses substances which are involved in modifying the immune response. Examples of immune response modifiers include such compounds as lymphokines, and the like. Lymphokines include, for example, tumor necrosis factor, interleukins 1, 2, and 3, lymphotoxin, macrophage activating factor, migration inhibition factor, colony stimulating factor, alpha-interferon, beta-interferon, gamma-interferon and their subtypes.

Administration of antigen or antigen-encoding nucleic acid molecule, polynucleotide or polypeptide, in the practice of invention methods will typically be by topical application. Accordingly, a "permeation enhancer" also can be included with electropulsing to increase introduction of a composition. As used herein, the term "permeation enhancer" refers to any action (e.g., mechanical, physical, chemical) or any composition that can increase or "augment" introduction of a composition into skin and/or muscle cells. The term "augment," when used herein as a modifier of introduction, means that the rate (over time) or amount of composition introduced into skin and/or muscle cells via electropulsing is greater than that produced by electropulsing in the absence of the permeation enhancer. Thus, administering a permeation enhancer prior to, substantially contemporaneously with or after topical application of a therapeutic agent serves to "augment" electrically induced introduction of the composition into skin and/or muscle cells. Alternatively, a permeation enhancer can be mixed with the composition in the pharmaceutical formulation to be introduced. Permeation enhancer compositions that increase the permeability of skin and/or muscle cells include, for example, alcohols (e.g., methanol), alkyl methyl sulfoxides (e.g., DMSO), pyrrolidones (e.g., 2-pyrrolidone), surfactants, urea, glycerol monolaurate, polyethylene glycol monolaurate, glycerol monolaurate, docainehydrochloride, hydrocortisone, menthol, methyl salicylate, and the like. Permeation enhancers further include mechanical or physical actions that function in association with an electrical impulse (e.g., abrasion, vibration, ultrasound, and the like).

Depending on the nature of the therapeutic agent, the desired depth of penetration, the target tissue type, and the like, it may be desirable to conduct electroporation in combination with other electrically-based treatment modalities. Electropulsing conducted substantially contemporaneously with iontophoresis (IPH), can produce a greater therapeutic effect than either applying the pulse or iontophoresis alone. Furthermore, electroincorporation (EI) (see, e.g., U.S. Pat. No. 5,464,386, which is hereby incorporated by reference herein in its entirety), or electropulsing in combination with IPH and liposomal formulation can enhance delivery significantly. (see, e.g., Badkar, et al., Drug Delivery 6 (1999) 111–115). Accordingly, in another embodiment of the present invention, electropulsing is used in conjunction with one or more of iontophoresis and electroincorporation.

As used herein, the term "transdermally introducing" and grammatical variations thereof, refers to the delivery of a composition into the skin, through/across the skin, or a combination thereof.

Targeting the cells of the skin for gene therapy or immune stimulation has several advantages. First of all, the epidermis is an accessible tissue, which simplifies approaches for introduction of an antigen or a transgene. Keratinocytes, the predominant cell type in the epidermis and hence the cellular target for gene transfer, form the outer-most barriers of the skin, making them amenable to in vivo manipulation. The accessibility of the epidermis raises the potential for use of non-invasive, topical methods for gene transfer. The epidermis is a stratified squamous epithelium consisting of a basal proliferating compartment and a suprabasal, differentiating compartment. By targeting gene transfer to the basal compartment, genes can be introduced into epidermal stem cells. Various treatment regimens are thus made possible. For example, single gene recessive disorders such as lamellar ichthyosis (LI) or X-linked ichthyosis (XLI) could be treated using the gene transglutaminase 1, or the gene for the steroid sulfatase arylsulfatase C, respectively. Epidermal stem cells give rise to basal, transiently amplifying cells, which have a limited capacity to divide. In turn, these cells give rise to the differentiating keratinocytes of the suprabasal epidermis. Thus, by achieving transgene expression in progenitor basal keratinocytes, methods for long-term, sustained gene therapy or immune stimualation are provided.

Keratinocytes function well as synthetic and secretory cells. Keratinocytes have been shown to synthesize and secrete in-vivo the products of transfected genes. Circulating transgene-derived proteins such as growth hormone (GH) (22 kD), ApoE (34 kD), and FIX (57 kD) have been detected in athymic mice bearing grafts of keratinocytes. This demonstrates that transgene products expressed in the epidermis can penetrate the basement membrane zone and reach the systemic circulation. Similarly, secreted proteins can be produced from transfected genes in muscle cells.

A means for administering a composition can optionally be included in the electrical apparatus, which can be used to administer the composition to the target tissue prior to, substantially contemporaneously with, or after applying an electric pulse, iontophoresis, vibration or ultrasound, in their various embodiments. Depending on the specific formulation, a composition can be incorporated into a patch reservoir (e.g., as a nicotine patch), which is then attached both to the electrode and the skin. Formulations employed for IPH are advantageously used in this manner.

As used in the above context, the term "substantially contemporaneously" means that the electric pulse and the composition are applied to the skin reasonably close together in time. Preferably, the composition is administered prior to or concurrently with electropulsing. When applying multiple electrical impulses, the composition can be administered before or after each of the pulses, or at any time between the electrical pulses. When applying any auxiliary electrically-based therapy (i.e., IPH, EI, and the like), vibration or ultrasound, the composition can be administered before or after each, and at any time between.

The apparatus and methods of the invention are also useful for cardiac applications (including catheters), restenosis, genes to grow new blood vessels, and the like. The bipolar wave form appears to reduce the risk of unintended ventricular fibrillation when the waveform is increased from DC to 10 kHz, for example. One of skill in the art would recognize that monitoring the heart using ECG recordings would show that there was no effect on the electrical rhythm of the heart. For example, the timing of the QRS complexes should appear not to differ during the train of the electroporation pulses, and no clinical disturbances of the cardiac rhythm should be observed. Administration of an agent, e.g., polynucleotides or drugs, by a method of the invention, alone or in combination with other compositions, for example that may be administered passively, is useful in various clinical situations. These include but are not limited to: 1) acute arterial thrombotic occlusion including coronary, cerebral or peripheral arteries; 2) acute thrombotic occlusion or restenosis after angioplasty; 3) reocclusion or restenosis after thrombolytic therapy (e.g., in an ishemic tissue); 4) vascular graft occlusion; 5) hemodialysis; 6) cardiopulmonary bypass surgery; 7) left ventricular cardiac assist device; 8) total artificial heart and left ventricular assist devices; 9) septic shock; and 10) other arterial thromboses (e.g., thrombosis or thromboembolism where current therapeutic measures are either contraindicated or not effective).

In another aspect of the invention, the described methods are useful for bypass grafts. These can include aortocoronary, aortoiliac, aortorenal, femoropopliteal. In the case of a graft with autologous or heterologous tissue, the cells in the tissue can be electroporated, ex vivo, with a nucleic acid encoding a protein of interest. Since electroporation is relatively fast, a desired nucleic acid can be transferred in a saphenous vein, e.g., outside the body, while the extracorporeal circulation in the patient is maintained by a heart-lung machine, and the vein subsequently grafted by standard methods. Where synthetic material is used as a graft, it can serve as a scaffolding where appropriate cells containing a nucleic acid sequence of interest that has been electroporated, ex vivo, can be seeded.

The method of the invention can be used to treat disorders by delivery of any composition, e.g., drug or gene with a catheter. For example, patients with peripheral arterial disease, e.g., critical limb ischemia (Isner, J. M. et al, Restenosis SummitVIII, Cleveland, Ohio, 1996, pp 208–289) can be treated as described herein. Both viral and non-viral means of gene delivery can be achieved using the method of the invention. These include delivery of naked DNA, DNA-liposome complex, ultraviolet inactivated HVJ (haematoagglutanating virus of Japan) liposome vector, delivery by particle gun (e.g., biolistics) where the DNA is coated to inert beads, etc. Various nucleic acid sequences encoding a protein of interest can be used for treatment of cardiovascular disorders, for example. The expression of the growth factors PDGF-B, FGF-1 and TGF-beta-1 has been associated with intimal hyperplasia, therefore, it may be desirable to either elevate (deliver sense constructs) or decrease (deliver antisense) such gene expression. For example, whereas PDGF-B is associated with smooth muscle cell (SMC) proliferation and migration, FGF-1 stimulates angiogenesis and TGF-beta-1 accelerates procollagen synthesis.

Any composition that inhibits SMC proliferation and migration, platelet aggregation and extracellular modeling is also desirable for use in the electroporation-mediated delivery method of the invention. Such compositions include interferon-.gamma. which inhibits proliferation and expression of alpha.-smooth muscle actin in arterial SMCs and non-protein mediators such as prostaglandin of the E series.

The following examples are intended to illustrate but not limit the invention. While they are typical of those that might be used, other procedures known to those skilled in the art may alternatively be used.

EXAMPLES

Example 1

Six volunteers were each exposed to four different electroporation signals. Each electroporation signal had a bipolar square waveform and a different frequency. The volunteers were asked to rate their degree of discomfort on a scale of 0 to 10 where 0 meant no pain and 10 was unbearable. The responses related to the same electroporation signals were averaged. FIG. 15 plots the averaged discomfort level versus the frequency of the electroporation signals. Increasing the signal frequency more than halved the discomfort level.

Example 2

HEp-2 (Epidermoid carcinoma of human larynx, ATCC CCL-23, passage no 350) were obtained from American Type Culture Collection, Rockville, Md. Cells were grown in Eagle's MEM (Gibco, BRL) supplemented with 10% FCS, 0.1 mM Non-essential Amino Acids, 1.0 mM Sodium pyruvate, and 1% L-glutamine in a 5% $CO_2$—air atmosphere at 37° C. Cells growing in an exponential phase were harvested by trypsinization and viability determined by trypan blue dye exclusion test. A cell suspension in culture medium was prepared at a concentration of 222,000 cells/ml and cells seeded in a 96 well plate at a final concentration of 40,000 cells per well. Cells were pulsed using 0.5 cm 6-needle hexagonal array electrodes 16 connected to a prototype bipolar pulse generator. The needle array was inserted in the well of a 96-well microplate and pulsed with the selected experimental parameters. The plates were incubated for 44 hrs in a 5% $CO_2$-air atmosphere at 37° C. before carrying out the XTT cell survival assay that is based on metabolic conversion of tetrazolium salts to formazan which is measured spectrophotometrically. Only living cells convert XTT to formazan. Optical density (O.D.) of each well was measured spectrophotometrically at 450 nm using a microplate reader (Packard, Model Spectra Count). The percent cell survival values are relative values calculated from the O.D. values of the sample, $[OD_{sample}]$, control with 100% cell survival (D–E–), $[OD_{100}]$, and control with 0% cell survival (D–E– with SDS), $[OD_0]$, using the formula: % cell survival=$([OD_{sample}]-[OD_0])/([OD_{100}]-[OD_0])\times 100$ Typical results showed that pulsed cells require lesser drug concentrations to be killed than non-pulsed cells. Compared to unipolar pulses, bipolar pulses 44 seem to be equal or better in terms of efficacy of cell killing.

Example 3

BALB/c A nu/nu mice were surgically implanted with HEp-2 tumors in a subcutaneous sac made in the right flank of nude mice. The tumors 34 were allowed to grow and were treated when their average size was about 80 mm$^3$. The drug, bleomycin, 0.5 units dissolved in 0.15 ml of saline, was injected in each mouse intratumorally using a 30 gauge needle. The drug was injected very slowly at the tumor base and the needle direction rotated (fanning technique) for uniform drug distribution in the tumor 34. The mice in the control were only pulsed D–E+; D=Drug, E=Electric field, +/–denote presence or absence, respectively) while those in the treated group were pulsed and received drug (D+E+). A time lapse of 10+/–1 minute was maintained between the drug injection and the application of electric pulse to allow bleomycin to spread uniformly throughout the tumor 34. The electrical pulses, generated by the prototype bipolar square wave pulse generator, were delivered to the tumor 34 through a 6-needle array (see for example, U.S. Pat. No. 5,702,359 herein incorporated by reference), inserted to the depth of the tumor 34. The muscle reaction to the treatment with bipolar square pulses was significantly reduced from what was achieved with monopolar square pulses. The mice in both the control and pulse-treated groups were monitored every day for mortality and sign of any other disease. The tumor response has been scored based on WHO guidelines as (a) Partial regression (PR) if the initial tumor volume decreased by at least 50%, (b) Complete regression (CR) if the tumor 34 became unpalpable and (c) Cure, if the CR achieved at a given tumor site was maintained at least 60 days after the first tumor treatment and the excised sample from the tumor area shows absence of tumor cells histopathologically.

FIG. 16 illustrates the results for the experimental and control groups. The Electroporation therapy of HEp-2 resulted in a severe early edema, and later necrosis of the tumor 34 in nearly all the mice treated by both the drug (D) and the pulse (E). The tumor volume of the mice in this treated group, D+E+, decreased, while those in the control group D–E+, showed substantial increase. In 87.5% (7/8) of the treated mice, complete tumor regression was observed 65 days following treatment, while 12.5% (1/8) showed partial (>80%) regression.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

What is claimed is:

1. An electroporation system comprising:
   a. an electroporation therapy apparatus comprising a body and a plurality of electrodes disposed in the body;
   b. a connector that provides electrical communication between the electrodes disposed in the body of the electroporation therapy apparatus and an electroporation instrument; and
   c. an electroporation instrument that delivers a therapeutic electrical signal, wherein the therapeutic electrical signal comprises an electroporation signal and an agent movement signal.

2. An electroporation system according to claim 1, wherein the electroporation signal has a bipolar waveform.

3. An electroporation system according to claim 1, wherein the electroporation signal has a bipolar square waveform.

4. An electroporation system according to claim 1, wherein the electroporation signal has a frequency of greater than about 10 kHz.

5. An electroporation system according to claim 1, wherein the agent movement signal has a monopolar waveform.

6. An electroporation system according to claim 1, wherein the agent movement signal adds a DC offset to the electroporation signal.

7. An electroporation system according to claim 1, wherein the agent movement signal has a voltage less than about 200 V.

8. An electroporation system according to claim 1, wherein the electroporation signal is provided by first electronics that include a first power source in communication with polarity switching electronics and the agent movement signal is provided by second electronics that include a second power source connected in series with the first power source.

9. An electroporation system according to claim 8, wherein the first power source and the second power source are each a DC power source.

10. An electroporation system according to claim 1, wherein the electroporation instrument has polarity switching electronics for changing a monopolar electrical signal to a bipolar electrical signal prior to delivering the therapeutic electrical signal to the electrodes of the electroporation therapy apparatus.

11. An electroporation system according to claim 10, wherein the polarity switching electronics include a plurality of switches.

12. An electroporation system according to claim 10, wherein the polarity switching electronics include a first pair of switches and a second pair of switches arranged in a bipolar H-Bridge.

13. An electroporation system according to claim 10, wherein a first power line and a second power line connect the polarity switching electronics to a power source and a first output line and a second output line connect the polarity changing electronics to the connector.

14. An electroporation system according to claim 10, wherein the polarity changing electronics include a plurality of switches configured to occupy a first configuration and a second configuration, in the first configuration the switches connect the first power line to the first output line and the second power line to the second output line and in the second configuration the switches connect the first power line to the second output line and the second power line to the first output line.

15. An electroporation system according to claim 14, further comprising a controller for moving the switches between the first configuration and the second configuration.

16. An electroporation system according to claim 10 further comprising a DC power source for adding a DC offset to the bipolar electrical signal.

17. An electroporation system according to claim 10 further comprising a controller for controlling the frequency of the bipolar signal.

18. An electroporation system according to claim 10 further comprising a crowbar for shorting a power supply of the electroporation instrument in response to detection of a fault condition.

19. An electroporation system according to claim 10, wherein a power source of the electroporation instrument includes a plurality of storage capacitors.

20. An electroporation system according to claim 10, further comprising electronics for monitoring the voltage of the bipolar signal.

21. An electroporation system according to claim 10, wherein the electrodes receive the bipolar electrical signal from the polarity switching electronics.

22. An electroporation system according to claim 10, wherein the bipolar electrical signal is a bipolar square waveform.

23. An electroporation system according to claim 22 further comprising a controller for controlling the frequency of the bipolar electrical signal.

24. An electroporation system according to claim 23, wherein the bipolar electrical signal has a frequency greater than about 10 kHz.

25. An electroporation instrument that generates a therapeutic electrical signal, comprising:
   a. first electronics for generating an electroporation signal;
   b. second electronics for generating an agent movement signal;
   c. a controller that controls generation of a therapeutic electrical signal, wherein the therapeutic electrical signal is a combination of an electroporation signal and the agent movement signal; and
   d. a connector for providing electrical communication of the therapeutic electrical signal from the electroporation instrument to an electroporation therapy apparatus connected thereto.

* * * * *